United States Patent
Kodama et al.

(10) Patent No.: US 11,191,487 B2
(45) Date of Patent: Dec. 7, 2021

(54) CONTACT STATE ESTIMATING DEVICE, AND BIOLOGICAL SIGNAL MEASURING DEVICE

(71) Applicant: ASAHI KASEI KABUSHIKI KAISHA, Tokyo (JP)

(72) Inventors: Kei Kodama, Tokyo (JP); Masashi Yamada, Tokyo (JP)

(73) Assignee: Asahi Kasel Kabushiki Kaisha, Tokyo (JP)

( * ) Notice: Subject to any disclaimer, the term of this patent is extended or adjusted under 35 U.S.C. 154(b) by 123 days.

(21) Appl. No.: 16/467,800

(22) PCT Filed: Nov. 28, 2017

(86) PCT No.: PCT/JP2017/042627
§ 371 (c)(1),
(2) Date: Jun. 7, 2019

(87) PCT Pub. No.: WO2018/105447
PCT Pub. Date: Jun. 14, 2018

(65) Prior Publication Data
US 2019/0320981 A1    Oct. 24, 2019

(30) Foreign Application Priority Data

Dec. 8, 2016    (JP) .............................. JP2016-238687

(51) Int. Cl.
*A61B 5/00* (2006.01)
*A61B 5/021* (2006.01)
(Continued)

(52) U.S. Cl.
CPC ........ *A61B 5/6844* (2013.01); *A61B 5/02108* (2013.01); *A61B 5/0531* (2013.01);
(Continued)

(58) Field of Classification Search
CPC . A61B 5/6844; A61B 5/02108; A61B 5/0408; A61B 5/0531; A61B 5/7425;
(Continued)

(56) References Cited

U.S. PATENT DOCUMENTS 3,784,908 A * 1/1974 Anderson .............. G01R 27/02
600/547
2012/0157867 A1* 6/2012 Pekonen .............. A61B 5/0006
600/509
(Continued)

FOREIGN PATENT DOCUMENTS

JP    2011-025071 A    2/2011
JP    2014-023711 A    2/2014
(Continued)

OTHER PUBLICATIONS

International Search Report dated Mar. 6, 2018, issued in corresponding International Patent Application No. PCT/JP2017/042627.
(Continued)

*Primary Examiner* — Amanda K Hulbert
*Assistant Examiner* — Philip C Edwards
(74) *Attorney, Agent, or Firm* — Morgan, Lewis & Bockius LLP

(57) ABSTRACT

A contact state estimating device includes: a first and a second electrode brought into contact with an object to be measured; a direct current voltage supply unit; a signal switching unit configured to switch a first pathway through which the direct current voltage supply unit supplies direct current voltage to the first electrode and an output signal from the second electrode is output and a second pathway through which the direct current voltage supply unit supplies direct current voltage to the second electrode and an output signal from the first electrode is output to each other; and a contact state estimating unit configured to estimate a contact
(Continued)

state of the first electrode or the second electrode with the object, based on the output signal acquired at a timing at which a pulse noise is anticipated to occur in association with switching between the first pathway and the second pathway.

19 Claims, 20 Drawing Sheets

(51) Int. Cl.
*A61B 5/0531* (2021.01)
*A61B 5/25* (2021.01)

(52) U.S. Cl.
CPC .............. *A61B 5/25* (2021.01); *A61B 5/7425* (2013.01); *A61B 2562/0219* (2013.01)

(58) Field of Classification Search
CPC ... A61B 2562/0219; A61B 5/25; A61B 5/681; A61B 5/7221; A61B 5/276
USPC ......................................................... 600/301
See application file for complete search history.

(56) References Cited

U.S. PATENT DOCUMENTS

| | | | |
|---|---|---|---|
| 2013/0317318 A1* | 11/2013 | Tartz | A61B 5/0531 600/301 |
| 2014/0316229 A1* | 10/2014 | Netti | A61B 5/6802 600/383 |
| 2015/0245782 A1* | 9/2015 | Morland | A61B 5/065 600/301 |
| 2016/0242672 A1* | 8/2016 | Mikoshiba | A61B 5/02416 |
| 2016/0270872 A1* | 9/2016 | Groberman | A61B 8/02 |
| 2017/0086699 A1 | 3/2017 | Shirai | |

FOREIGN PATENT DOCUMENTS

| | | |
|---|---|---|
| JP | 2015-150182 A | 8/2015 |
| WO | 2015/056434 A1 | 4/2015 |
| WO | 2016/125214 A1 | 8/2016 |

OTHER PUBLICATIONS

International Preliminary Report on Patentability dated Jun. 11, 2019, for the corresponding International Application No. PCT/JP2017/042627.

* cited by examiner

FIRST PATHWAY

SECOND PATHWAY

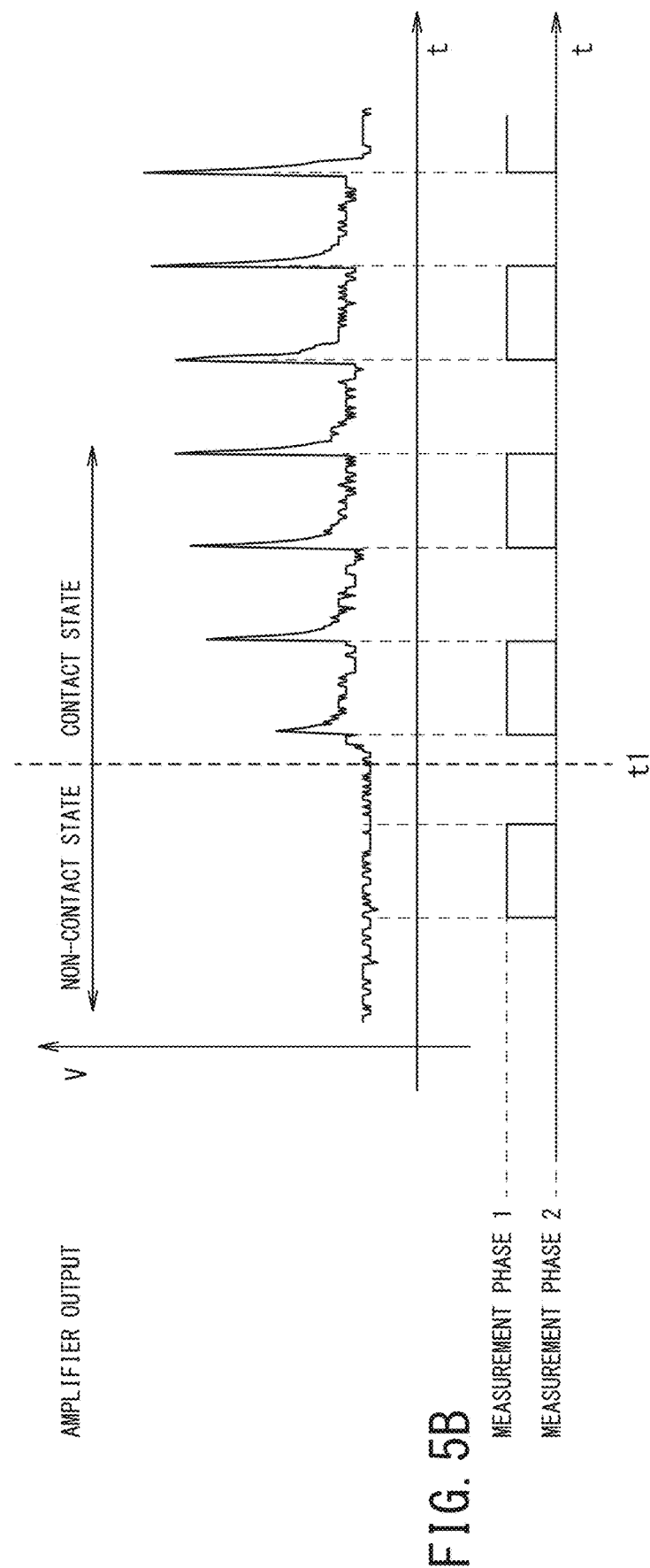

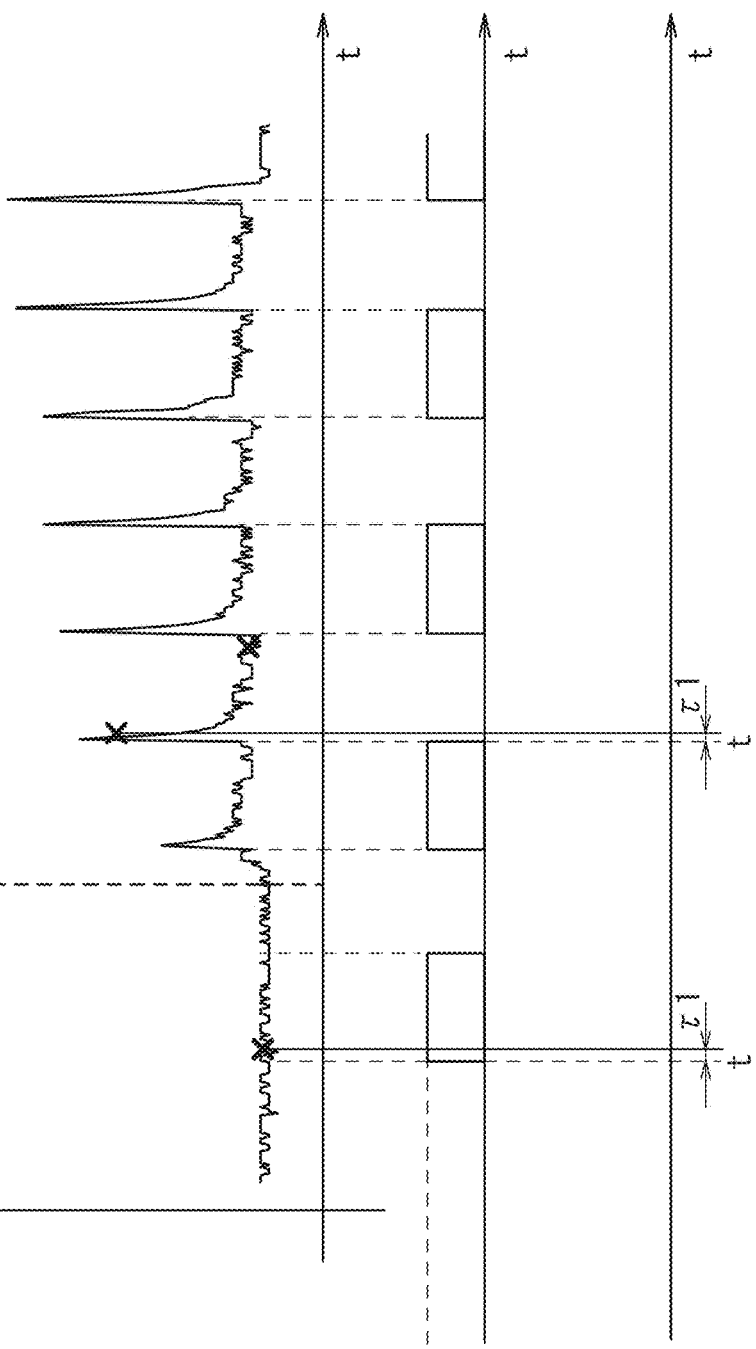

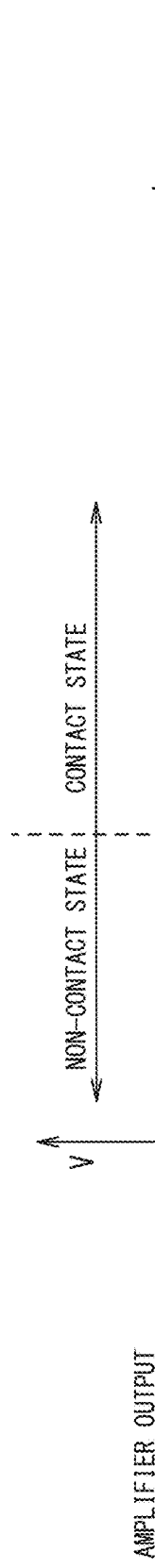
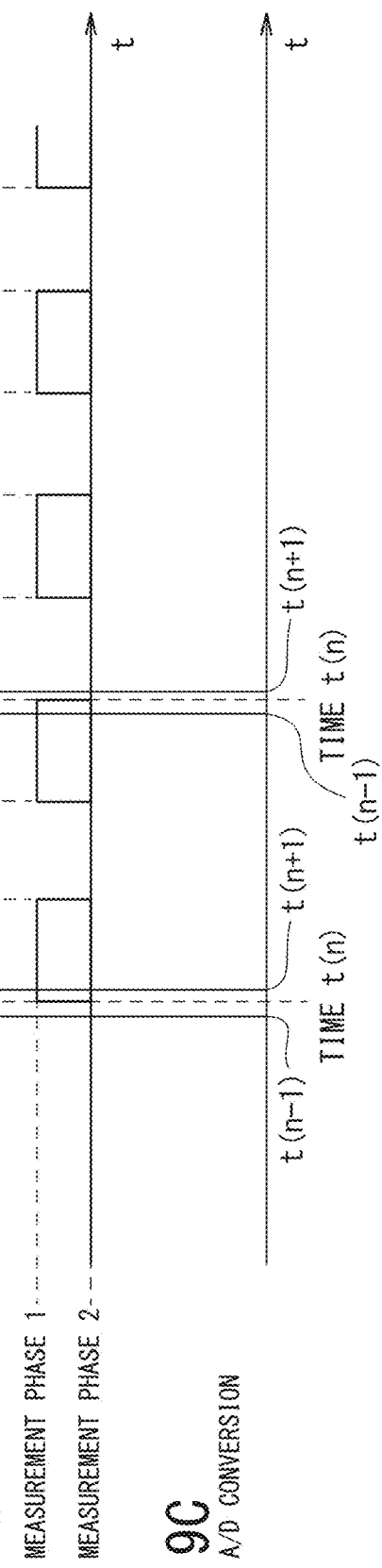

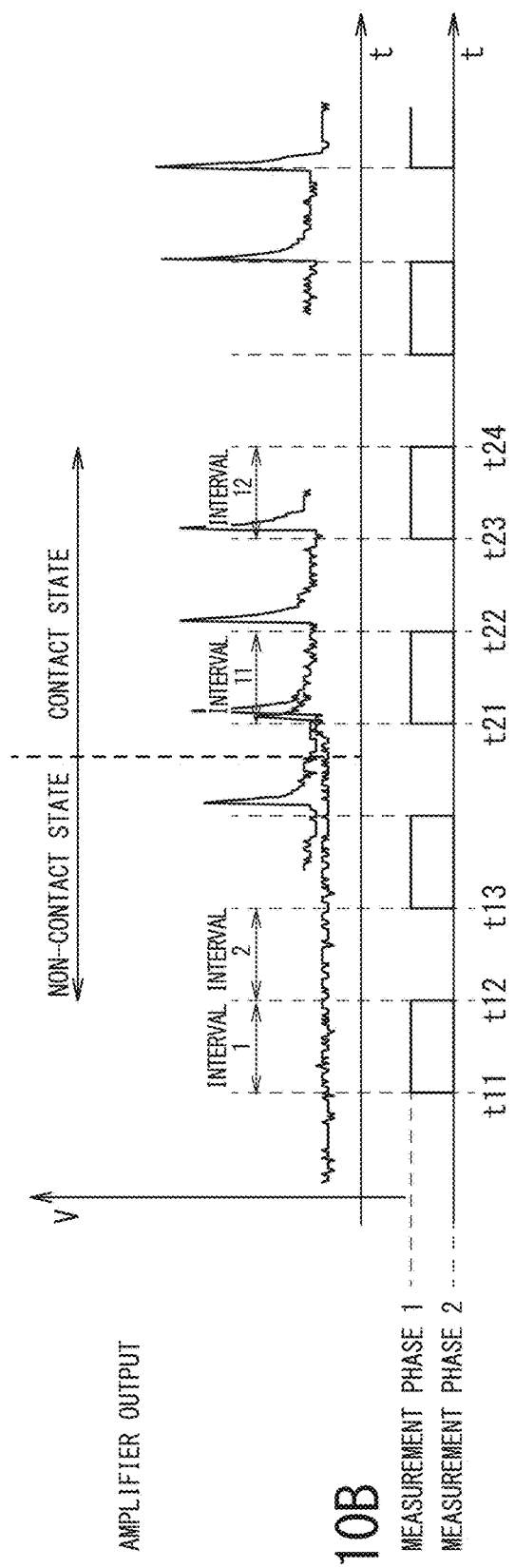

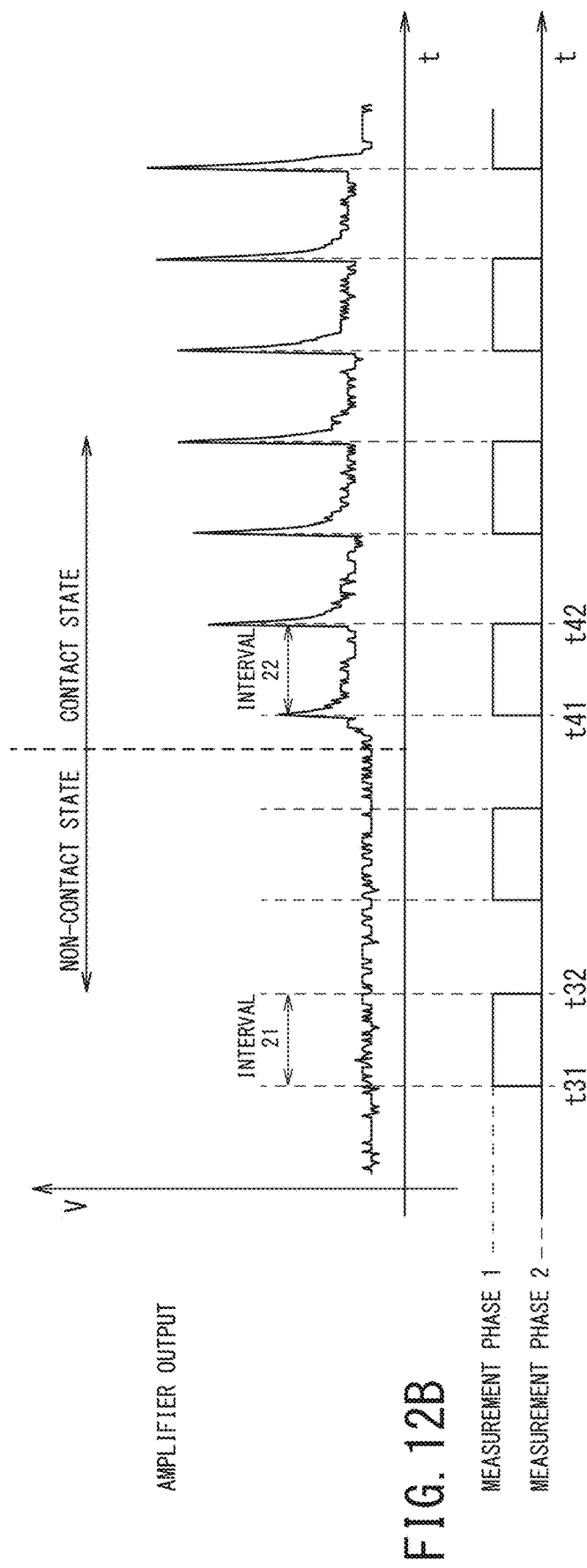

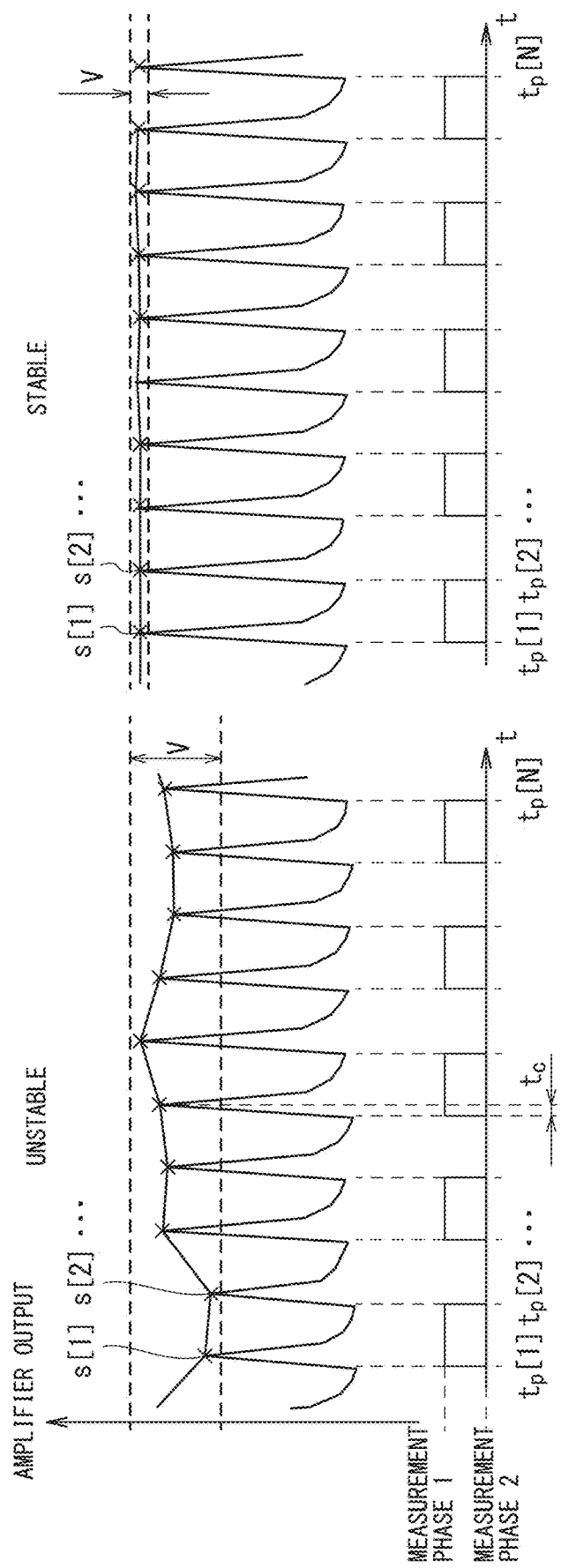

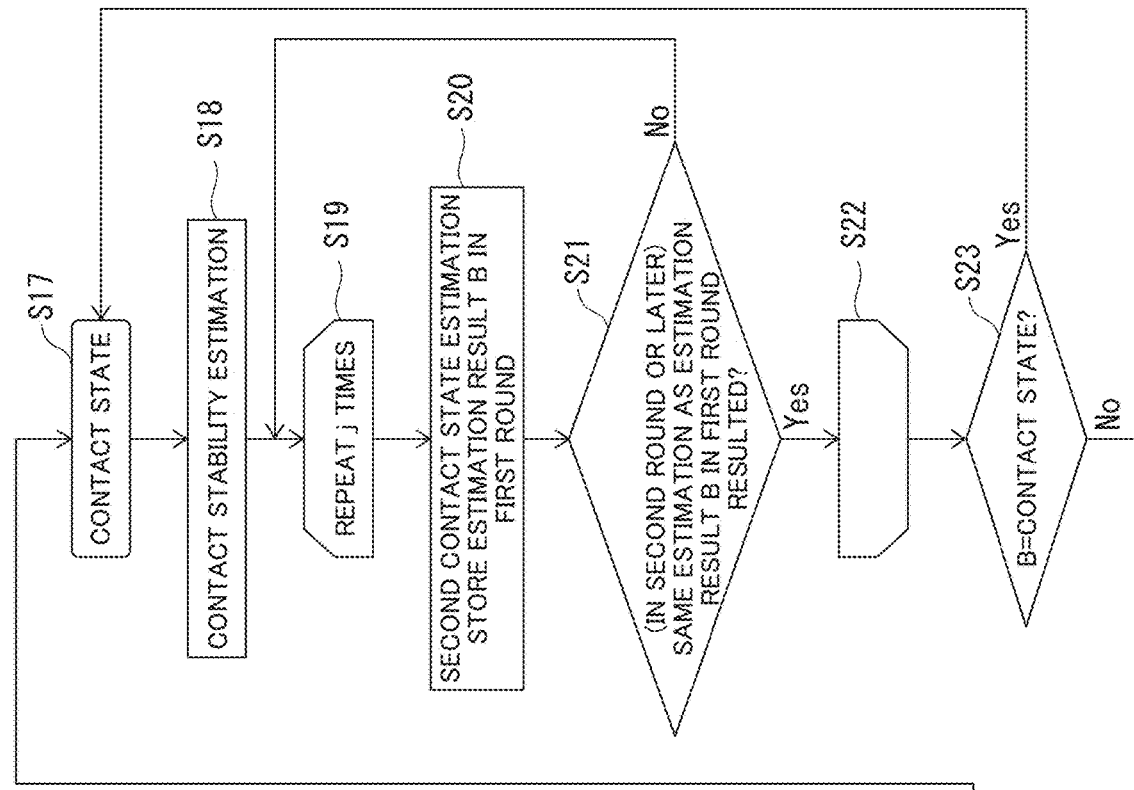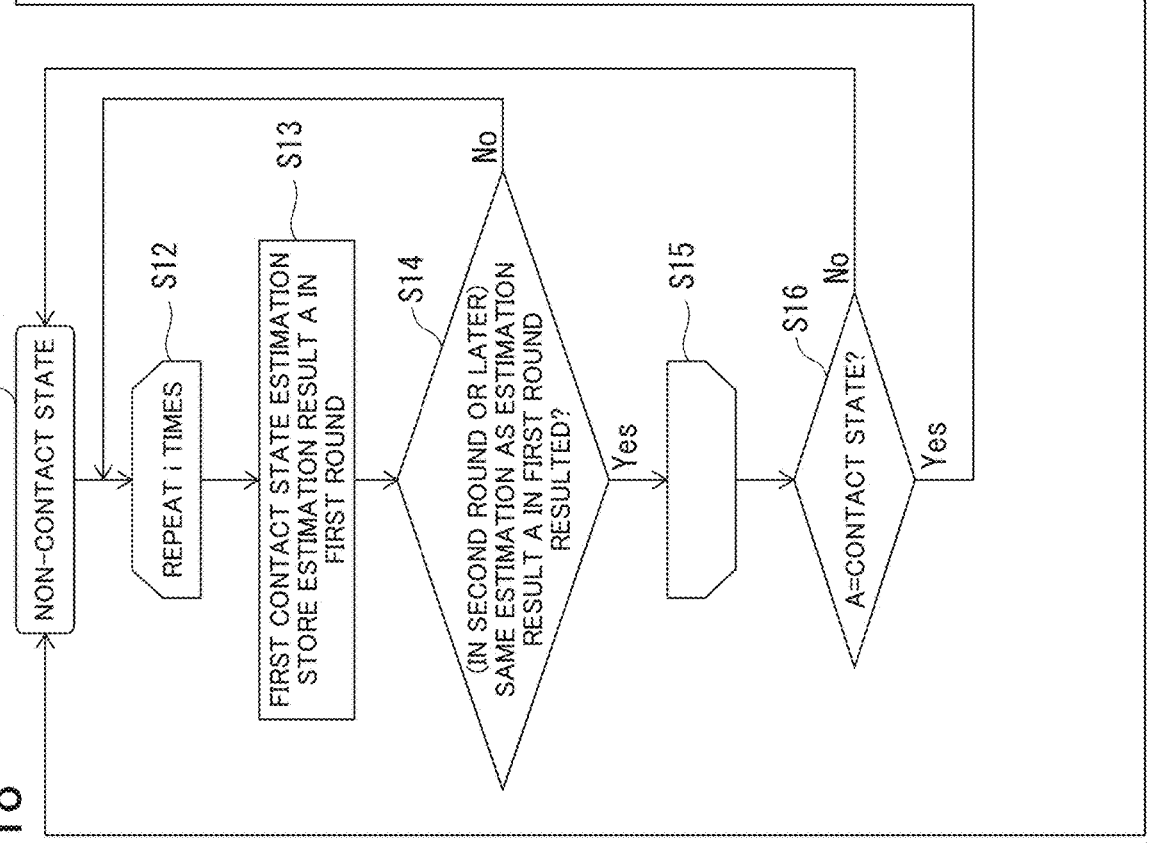
FIG. 18

CONTACT STATE ESTIMATING DEVICE, AND BIOLOGICAL SIGNAL MEASURING DEVICE

TECHNICAL FIELD

The present invention relates to a contact state estimating device and a biological signal measuring device.

BACKGROUND ART

Conventionally, devices that are attached to a human body and measure biological signals have been known. For example, devices each of which has a watch-like shape, is worn on the wrist, measures a pulse of the wearer, and provides information representing an activity amount have been proposed. As examples of such a watch-like device, HR-500U manufactured by OMRON Corporation and PS-500B manufactured by Seiko Epson Corporation are sold in Japan.

A device for performing pulse measurement (hereinafter, also referred to as a pulse measuring device) as described above is configured to irradiates the skin of a human body with green light or red light and receive reflected light of the radiated light with a light receiving element. Such pulse measuring devices often use a principle of, using a characteristic that a portion of radiated light with which a human body is irradiated is absorbed by oxygenated hemoglobin in arterial blood, detecting pulsation of the arterial vessel, which occurs substantially in synchronization with a heartbeat, in the form of change in the amount of reflected light. Such a pulse measuring device has a possibility of, when the device is not worn on a human body, receiving outside light instead of non-existent reflection of radiated light by the human body and, when the outside light is fluorescent light, detecting radiated light fluctuation due to flickering of the fluorescent light, which occurs therein in principle, and incorrectly detecting the fluctuation as pulse fluctuation. Even when there is no flickering of outside light, there is a possibility that, because the pulse measuring device amplifies and detects noises in the light receiving element and electronic circuits at downstream stages, the pulse measuring device incorrectly detects the noises as pulse fluctuation.

Meanwhile, devices each of which, as with the above biological signal measuring devices, has a watch-like shape, is worn on a wrist, and measures impedance or conductivity between two electrodes, with which the casing is provided and which are in contact with the skin, have been known. Such devices are often required to have a function of estimating whether the electrodes and the skin are in a contact state or in a non-contact state with each other.

For example, PTLs 1 and 2 disclose methods of, based on the fact that, when electrodes are attached to a human body, resistance between conductors decreases, flowing current between the conductors, detecting a voltage drop, and, based on the detected voltage drop, estimating whether the electrodes and the human body are in a contact state or in a non-contact state with each other.

Further, as a measuring device configured to measure skin conductance by applying direct current voltage as described above, a measuring device configured to, by switching pathways through which voltage is applied to two electrodes, obtain a measurement signal of skin conductance in which influence from polarization is suppressed is proposed (see, for example, PTL 3).

CITATION LIST

Patent Literature

PTL 1: JP 2015-150182 A
PTL 2: WO 2015/056434
PTL 3: JP 2014-23711 A

SUMMARY OF INVENTION

Technical Problem

However, there are large differences in skin conductivity of a human body among individuals, and, in a case of having naturally dry skin, being winter, or the like, there is a possibility that values of skin conductivity are measured to be small in spite of electrodes being in contact with a human body and the electrodes are therefore incorrectly estimated to be not in contact with the human body.

Further, there is a problem in that, since measurement values of skin conductivity fluctuate according to size of constituent electrodes, a threshold value optimum for determination of whether the electrodes are in a contact state or in a non-contact state differs every time the size of the electrodes is changed.

In addition, a biological signal measuring instrument for measuring a biological signal by coming into contact with a living body sometimes comes to have an unstable contact state due to movement of the living body, which causes the contact state between the living body and the biological signal measuring instrument to change. When the contact state changes in this manner, the change appears in an output signal as a noise, which makes it difficult to discriminate a biological signal therefrom.

The present invention is made in consideration of the above-described problems and an object of the present invention is to provide a contact state estimating device and a biological signal measuring device that are capable of, in a measuring device for measuring a biological signal by being attached to a human body, determining whether electrodes are in a contact state or in a non-contact state with high accuracy without being affected by a contact environment, such as a dry state of the skin and size of the electrodes.

Solution to Problem

In order to achieve the object mentioned above, according to an aspect of the present invention, there is provided a contact state estimating device including: a first electrode and a second electrode brought into contact with a living body serving as an object to be measured; a direct current voltage supply unit; a signal switching unit configured to switch a first pathway through which the direct current voltage supply unit supplies direct current voltage to the first electrode and an output signal from the second electrode is output and a second pathway through which the direct current voltage supply unit supplies direct current voltage to the second electrode and an output signal from the first electrode is output to each other; and a contact state estimating unit configured to estimate a contact state of the first electrode or the second electrode with the living body, based on the output signal acquired at a timing at which a pulse noise is anticipated to occur in association with a signal switching operation to switch the first pathway and the second pathway to each other.

According to another aspect of the present invention, there is provided a biological signal measuring device including: the contact state estimating device according to the aspect of the present invention; a biosensor configured to acquire a biological signal from a living body; and a biological information output unit configured to output biological information, based on the biological signal transmitted by the biosensor.

According to still another aspect of the present invention, there is provided a contact state estimating method including: fora first electrode and a second electrode brought into contact with a living body serving as an object to be measured, switching a first pathway through which a direct current voltage supply unit supplies direct current voltage to the first electrode and an output signal from the second electrode is output and a second pathway through which the direct current voltage supply unit supplies direct current voltage to the second electrode and an output signal from the first electrode is output to each other; acquiring the output signal at a timing at which a pulse noise is anticipated to occur in association with a signal switching operation to switch the first pathway and the second pathway to each other; and based on the output signal, estimating a contact state of the first electrode or the second electrode with the living body.

According to yet another aspect of the present invention, there is provided a contact state estimating program causing a computer to perform a contact state estimating method according to the still another aspect of the present invention.

According to a further aspect of the present invention, there is provided a medium storing a contact state estimating program according to the yet another aspect of the present invention.

Advantageous Effects of Invention

One aspect of the present invention enables discrimination between a contact state and a non-contact state of a sensor with a living body to be estimated with high accuracy without being affected by a contact environment, such as a dry state of the skin and size of the electrodes.

BRIEF DESCRIPTION OF DRAWINGS

FIGS. 5A and 5B are waveform charts illustrative of an example of an amplifier output associated with signal switching;

FIGS. 8A to 8C are explanatory diagrams fora description of an estimation method of a contact state;

FIGS. 9A to 9C are explanatory diagrams fora description of another estimation method of a contact state;

FIGS. 10A and 10B are explanatory diagrams for a description of still another estimation method of a contact state;

FIGS. 12A and 12B are explanatory diagrams for a description of still another estimation method of a contact state;

FIGS. 14A and 14B are explanatory diagrams for a description of an estimation method of contact stability;

FIG. 18 is a flowchart descriptive of an example of another contact state estimating method;

DESCRIPTION OF EMBODIMENTS

In the following detailed description, many specific concrete configurations are described so as to provide the complete understanding of embodiments of the present invention. However, it is apparent that the invention is not limited to such specific concrete configurations and other embodiments can be embodied. In addition, the following embodiments do not limit the invention according to CLAIMS but include all the combinations of characteristic configurations described in the embodiments.

Hereinafter, with reference to the drawings, an embodiment of the present invention will be described. In the following description of the drawings, the same signs are assigned to the same constituent components. However, the drawings are schematic, where a relation between thickness and planar dimensions, ratios of thickness among respective layers, and the like are different from actual ones.

First Embodiment

First, an example of a contact state estimating device according to a first embodiment of the present invention will be described.

Figure 1:
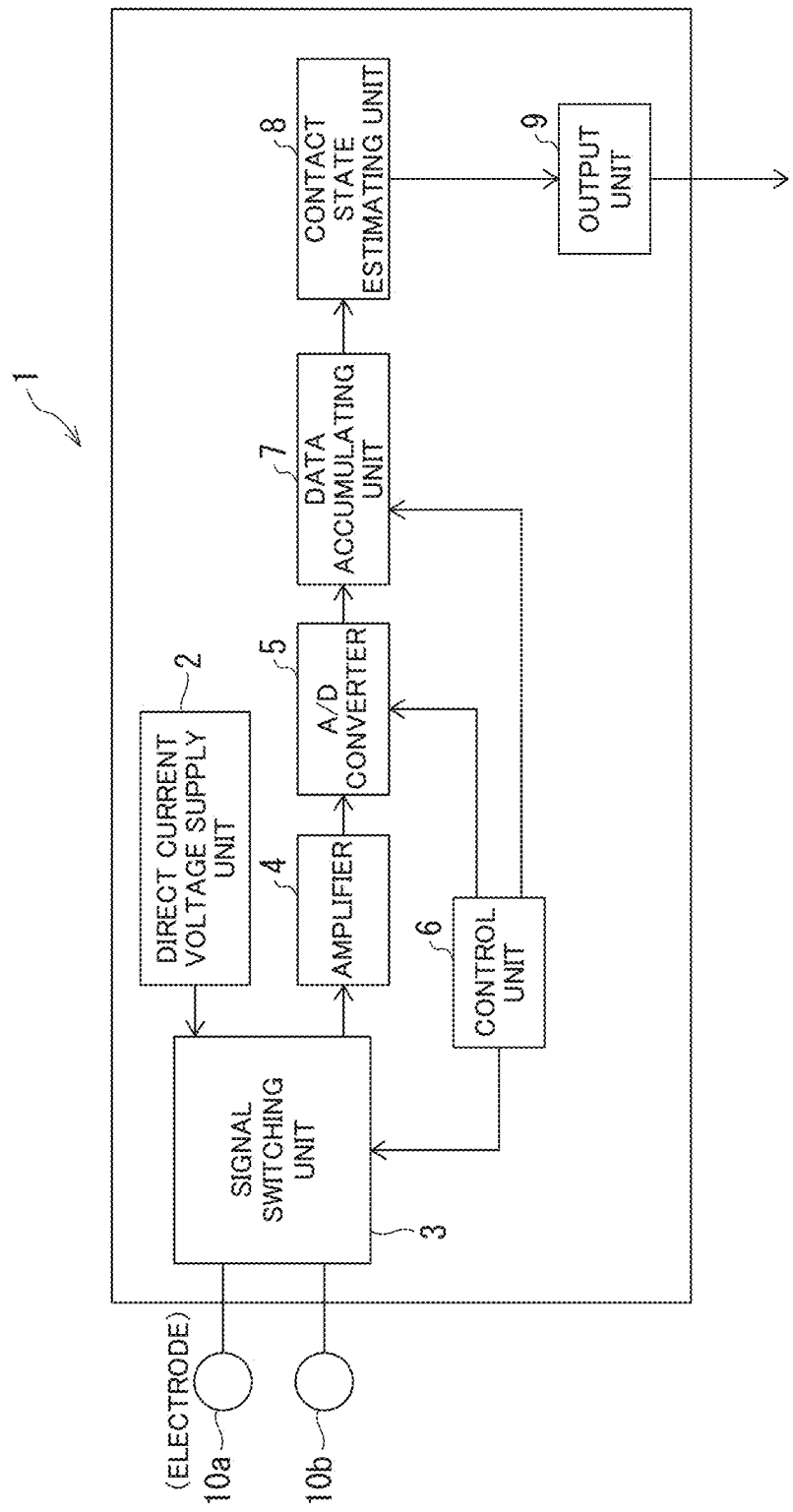
FIG. 1 is a block diagram illustrative of an example of a contact state estimating device according to a first embodiment of the present invention.

FIG. 1 is a block diagram illustrative of an example of a contact state estimating device 1 according to the present invention.

The contact state estimating device 1 includes a direct current voltage supply unit 2, such as a direct current voltage source, a signal switching unit 3, an amplifier 4, an A/D converter 5, a control unit 6, a data accumulating unit 7, a contact state estimating unit 8, and an output unit 9 and further includes a pair of electrodes 10a and 10b that are brought into contact with a living body, such as a human body. The contact state estimating device 1 estimates whether or not the electrodes 10a and 10b are in contact with the living body and outputs a result from the estimation.

The direct current voltage supply unit 2 applies direct current voltage to the signal switching unit 3.

The signal switching unit 3 switches connection destinations of the electrodes 10a and 10b between the direct current voltage supply unit 2 and the amplifier 4. That is, the signal switching unit 3 forms a first pathway that brings the electrodes 10a and 10b into conduction with the direct current voltage supply unit 2 and an input unit of the amplifier 4, respectively, or a second pathway that brings the electrodes 10b and 10a into conduction with the direct current voltage supply unit 2 and the input unit of the amplifier 4, respectively. The signal switching unit 3 switches the first pathway and the second pathway to each other at an arbitrary timing in response to a switching signal from the control unit 6.

The amplifier 4 accepts input of an output signal from the signal switching unit 3 and amplifies and outputs the input signal.

The A/D converter 5 accepts input of an output signal from the amplifier 4 (hereinafter, also referred to as an amplifier output) in conjunction with a timing signal instructing execution of A/D conversion from the control unit 6 and performs A/D conversion on the amplifier output at a timing at which, for example, the timing signal is input. A/D converted values to which the amplifier output is converted by the A/D converter 5 are accumulated in the data accumulating unit 7.

The control unit 6 outputs a switching signal instructing the signal switching unit 3 to switch the first pathway and the second pathway to each other to the signal switching unit 3 and therewith outputs, to the data accumulating unit 7, a time at which the switching signal is output as switching time information. The control unit 6 also outputs a timing signal instructing execution of A/D conversion to the A/D converter 5 at a predetermined timing, such as at a preset constant period, and therewith outputs, to the data accumulating unit 7, a time at which the timing signal is output as A/D conversion time information.

The data accumulating unit 7 accepts input of and successively accumulates the A/D converted amplifier output, which is output from the A/D converter 5, the switching time information, output from the control unit 6, and the A/D conversion time information, output from the control unit 6. On this occasion, the data accumulating unit 7 accumulates the A/D conversion time information and the amplifier output that was A/D converted by the A/D converter 5 at a timing at which the A/D conversion time information was output in association with each other.

Although, in the accumulation, a time at which a timing signal is output is used as A/D conversion time information, the A/D conversion time information can be information that represents timings at which A/D conversion is performed in a time series. For example, when timing signals are output from the control unit 6 at constant periods, the A/D conversion time information may be sequential numbers. In addition, although a time at which a switching signal is output is used as switching time information, the switching time information can be information that can represent timings of A/D conversion and output timings of switching signals in a time-series manner.

The contact state estimating unit 8 reads accumulated data accumulated in the data accumulating unit 7, estimates whether the electrodes 10a and 10b and the living body are in a contact state or the living body and both or either of the electrodes 10a and 10b are in a non-contact state with each other based on the read accumulated data, and outputs an estimation result.

The output unit 9 accepts input of the estimation result from the contact state estimating unit 8 and outputs the input estimation result to the outside. Although a case where the output unit 9 has a function of outputting an estimation result to the outside is described in the embodiment, the configuration is not limited to the case. The contact state estimating device 1 may be configured to, by using an output unit having a display function as the output unit 9 or further disposing a display unit performing display based on output from the output unit 9, display information, such as an estimation result of a contact state, within the contact state estimating device 1 instead of outputting information including an estimation result and the like to the outside. Further, the contact state estimating device 1 may also be configured to display within the contact state estimating device 1 and therewith output to the outside information, such as an estimation result of a contact state.

Figure 2:
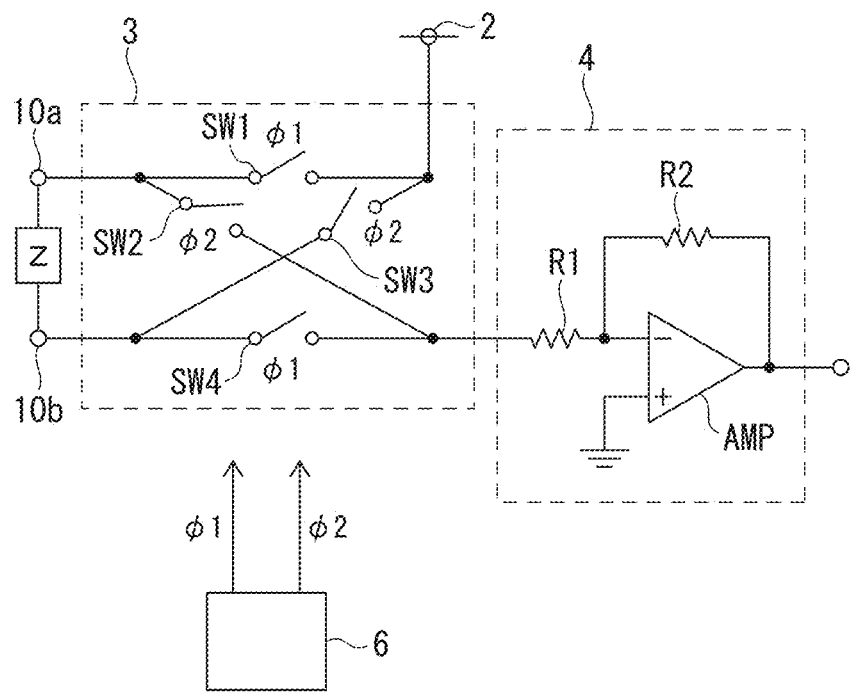
FIG. 2 is a circuit diagram illustrative of an example of a signal switching unit and an amplifier.

FIG. 2 is a diagram illustrative of an example of a circuit configuration of the signal switching unit 3 and the amplifier 4 in FIG. 1.

Figure 3A:
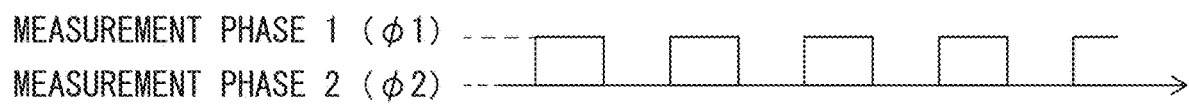
FIGS. 3A to 3C are explanatory diagrams provided for description of operations of the signal switching unit.

The signal switching unit 3 includes four switches SW1 to SW4, and the switches SW1 to SW4 operate in response to switching signals Φ1 and Φ2 from the control unit 6. The switches SW1 and SW2 are connected between the electrode 10a and the direct current voltage supply unit 2 and between the electrode 10a and the inverting input of the amplifier 4, respectively. The switches SW3 and SW4 are connected between the electrode 10b and the direct current voltage supply unit 2 and between the electrode 10b and the inverting input of the amplifier 4, respectively. The control unit 6 outputs the switching signal Φ1 for forming the first pathway in a measurement phase 1 to the switches SW1 and SW4. The control unit 6 also outputs the switching signal Φ2 for forming the second pathway in a measurement phase 2 to the switches SW2 and SW3. The control unit 6 outputting the switching signals Φ1 and Φ2, each of which, for example, brings a switch into conduction when the switching signal is at a HIGH level, in such a way that the switching signals alternately turn to the HIGH level as illustrated in FIG. 3A causes the signal switching unit 3 to alternately switch to the measurement phase 1 in which the first pathway is formed and the measurement phase 2 in which the second pathway is formed.

Figure 3B:
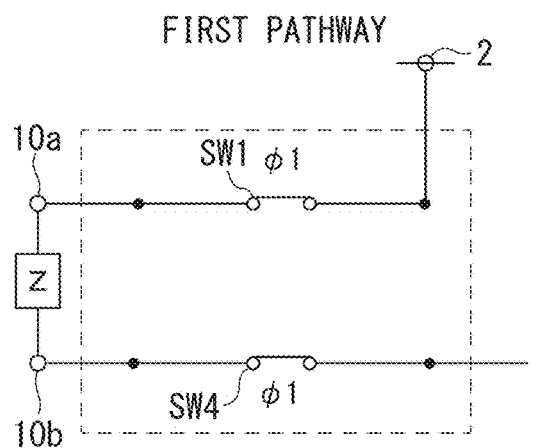
Figure 3C:
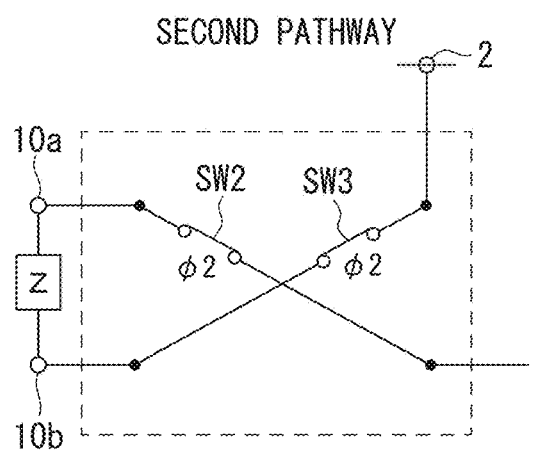

That is, when, while the electrodes 10a and 10b are in a state of being in contact with a human body, the switching signals Φ1 and Φ2 are at the HIGH level and a LOW level, respectively, the switches SW1 and SW4 and the switches SW2 and SW3 are in a conductive state and an open state, respectively, as illustrated in FIG. 3B. Thus, the first pathway in which the direct current voltage supply unit 2, the switch SW1, the electrode 10a, the electrode 10b, the switch SW4, and the amplifier 4 are connected in this sequence is formed. When the switching signals Φ1 and Φ2 are at the LOW level and the HIGH level, respectively, the switches SW2 and SW3 and the switches SW1 and SW4 are in a conductive state and an open state, respectively, as illustrated in FIG. 3C. Thus, the second pathway in which the direct current voltage supply unit 2, the switch SW3, the electrode 10b, the electrode 10a, the switch SW2, and the amplifier 4 are connected in this sequence is formed. A reference sign Z between the electrodes 10a and 10b denotes a variable impedance that changes mainly in association with sweat gland activity.

Returning to FIG. 2, the amplifier 4 is constituted by a differential amplifier circuit that includes, for example, an operational amplifier AMP, a resistor R1 the one end of which is connected to the inverting input terminal of the operational amplifier AMP, and a resistor R2 that is connected between the output terminal and the inverting input terminal of the operational amplifier AMP. The other end of the resistor R1 is connected to one ends of the switches SW2 and SW4.

Figure 4A:
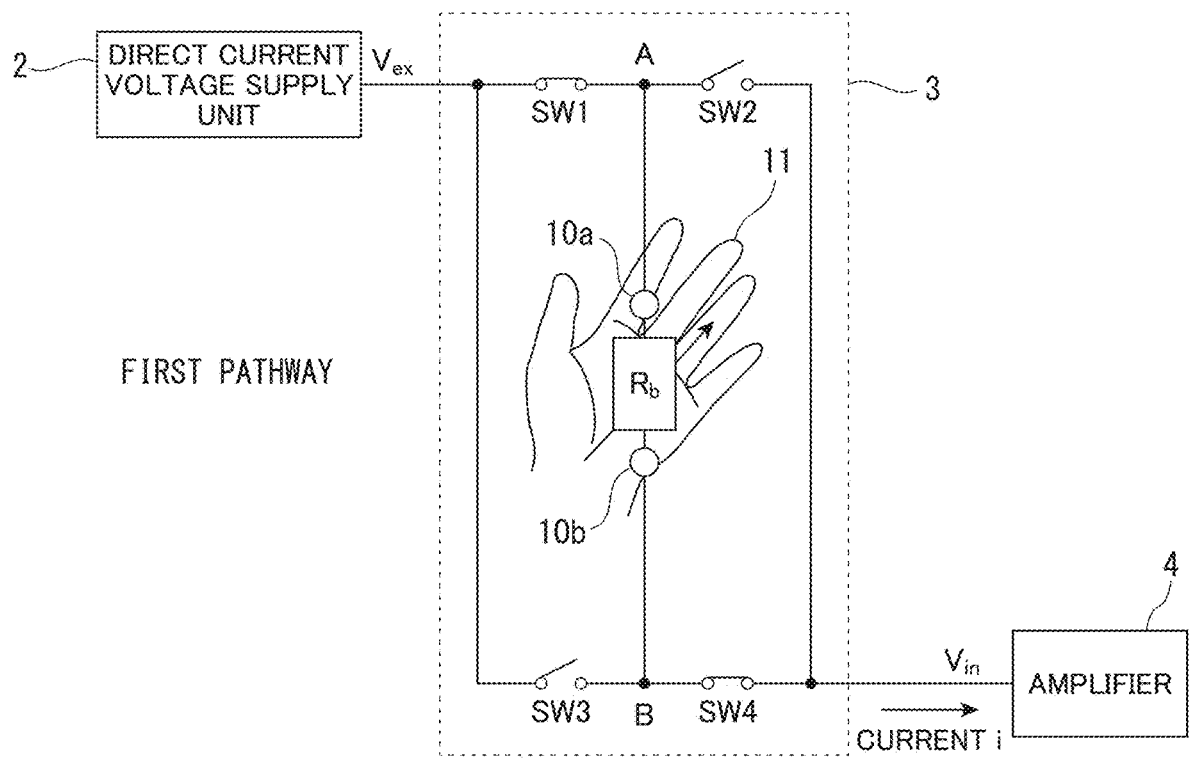
FIGS. 4A to 4B are other explanatory diagrams provided for description of the operations of the signal switching unit.
Figure 4B:
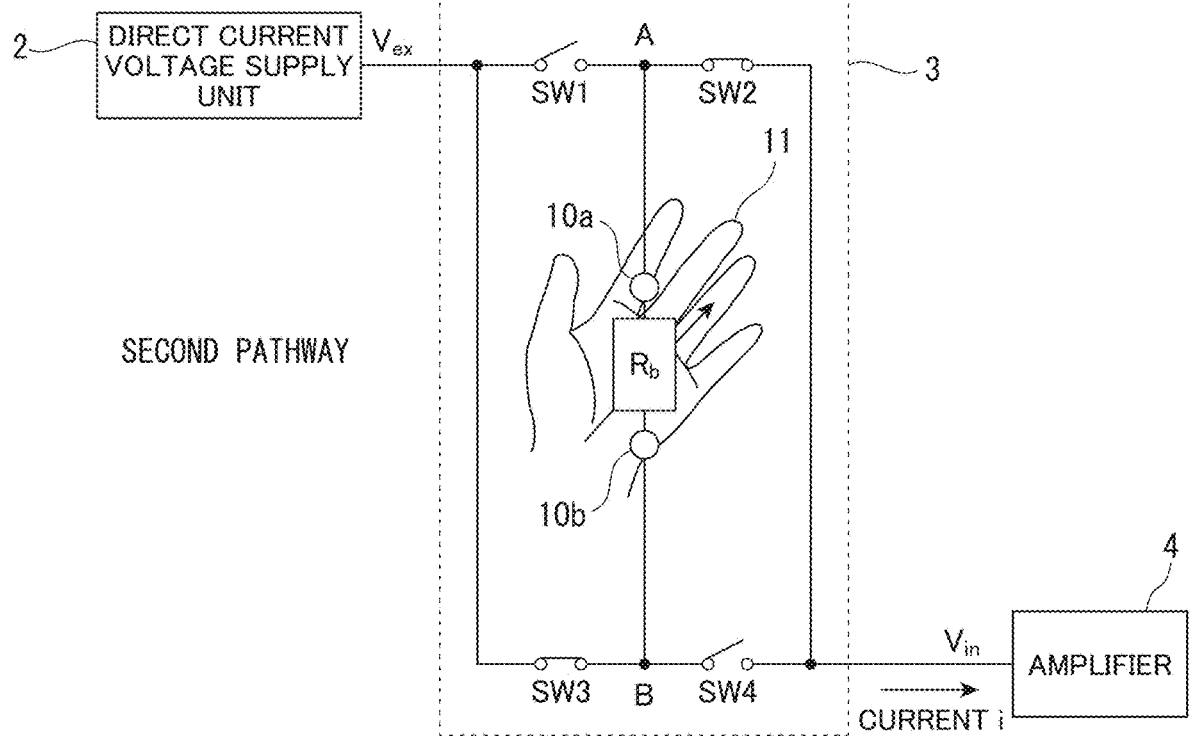

FIGS. 4A and 4B illustrate examples of an equivalent circuit of the skin of a living body. FIGS. 4A and 4B are diagrams illustrative of circuits in the measurement phases 1 and 2, in which the first and second pathways are formed, respectively. A reference sign 11 in FIGS. 4A and 4B indicates an object to be measured, for example, the skin of a human body. A reference sign $R_b$ in FIGS. 4A and 4B denotes conductance (equivalent to the variable impedance Z in FIGS. 3A to 3C) of the object 11 to be measured.

FIGS. 5A and 5B illustrate a waveform of an amplifier output when, using a measurement setup as illustrated in FIGS. 4A and 4B, the switches SW1 to SW4 are switched in the signal switching unit 3. In FIGS. 5A and 5B, the abscissa represents time. FIGS. 5A and 5B illustrate voltage at the output end of the amplifier 4, that is, an amplifier output, and the measurement phases, respectively. Waveforms in periods before and after a time point t1 indicate waveforms when the electrodes 10a and 10b are not in contact with and are in contact with the object 11 to be measured, respectively.

When the object 11 to be measured and the electrodes 10a and 10b are in contact with each other, the amplifier output rapidly increases when the signal switching unit 3 switches the first pathway and the second pathway to each other and subsequently gradually decreases. This phenomenon is caused by capacitance components between the object 11 to be measured and the electrodes 10a and 10b.

Figure 6:
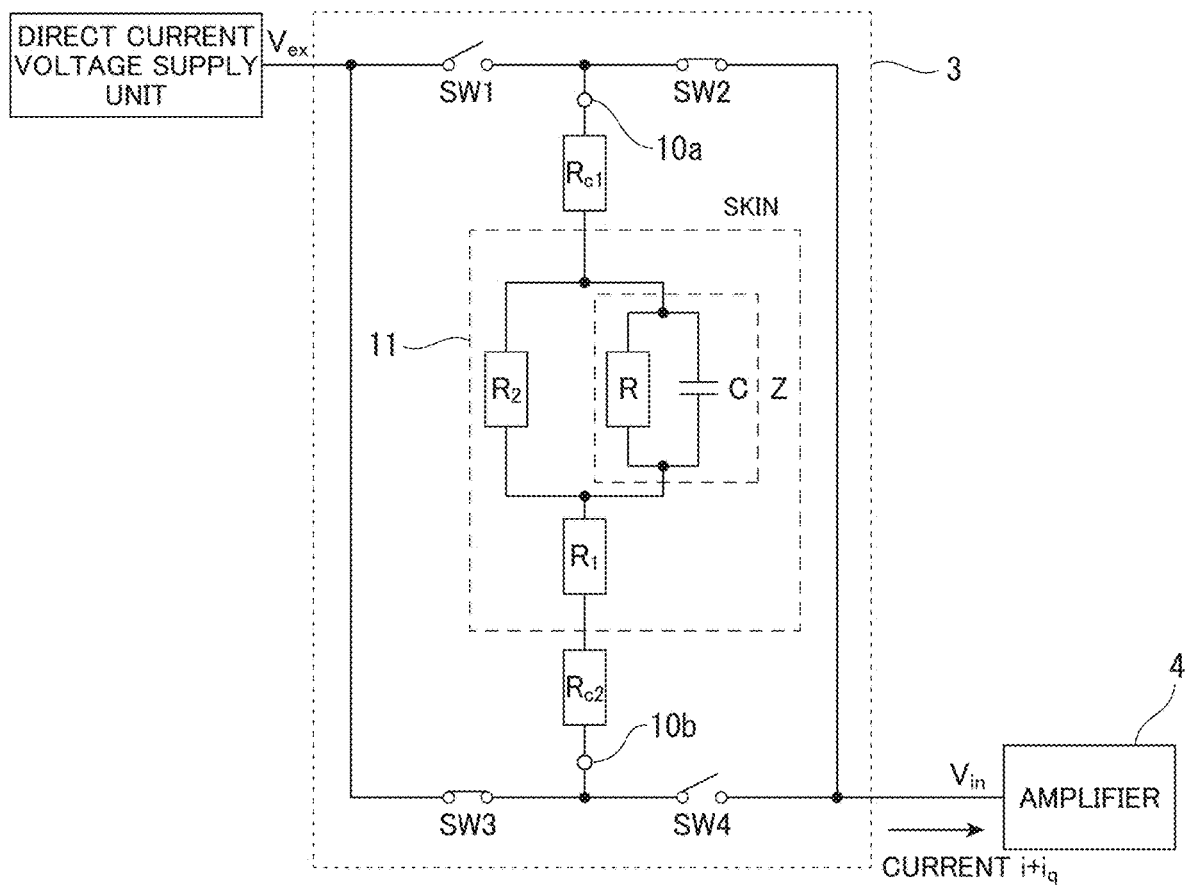
FIG. 6 is an example of an equivalent circuit of the skin of a living body.

FIG. 6 is a diagram in which, in the measurement system illustrated in FIGS. 4A and 4B, the object 11 to be measured, that is, the skin of a living body, which is in contact with the electrodes 10a and 10b, is replaced with an equivalent circuit. In FIG. 6, $R_1$, $R_2$, and Z denote a resistance of the dermis, a resistance of the epidermis, and a variable impedance, respectively, of the skin. In addition, $R_{c1}$ and $R_{c2}$ denote contact resistances between the electrodes 10a and 10b and the skin, respectively.

It is now assumed that the circuit is in a state in which the second pathway, in which the switches SW2 and SW3 are closed and the switches SW1 and SW4 are opened, is formed and voltage $V_{in}$, and voltage $V_{ex}$ are applied to the electrodes 10a and 10b, respectively ($V_{ex} > V_{in}$). From the electrode 10b to the electrode 10a, current i, which is expressed as $I = (V_{ex} - V_{in})/(R_1 + ((R \times R_2)/(R + R_2)))$, flows. In addition, in capacitance C, electric charge Q, which is expressed as $Q = C(V_{ex} - V_{in})$, is stored. A case where, when the circuit is in this state, by switching the signal switching unit 3, that is, closing and opening the switches SW1 and SW4 and the switches SW2 and SW3, respectively, the circuit is switched to the first pathway and the voltage applied to the skin is reversed is considered. Then, current $i_q$ flows out from the electrode 10a to the electrode 10b due to discharge of the electric charge Q having been charged in the capacitance C and, subsequently, current values due to the discharge gradually decrease. In consequence, a pulse noise as illustrated in FIGS. 5A and 5B is generated.

Figure 7:
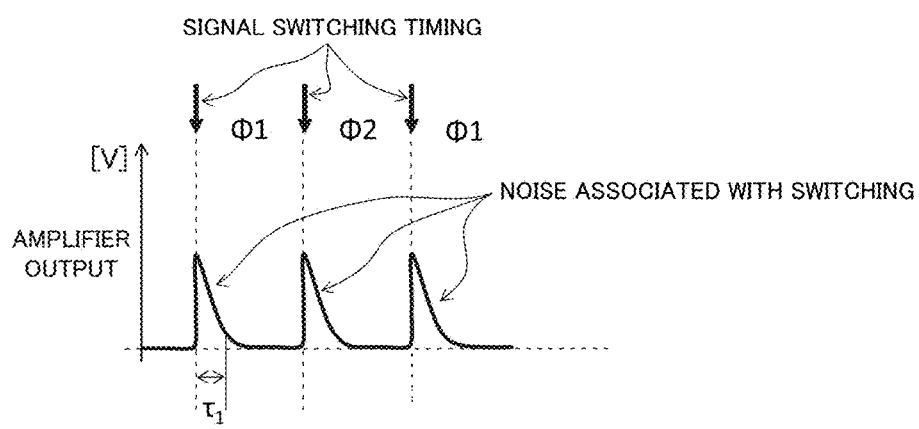
FIG. 7 is a diagram modeling a waveform of an amplifier output associated with signal switching.

The pulse noise has a characteristic of, as illustrated in FIG. 7, steeply increasing immediately after signal switching and subsequently decreasing to a constant voltage over a certain period of time.

In the contact state estimating device 1 according to the first embodiment of the present invention, by use of a characteristic that such a pulse noise occurs when the electrodes are in contact with a living body and does not occur when the electrodes are not in contact with the living body, whether the electrodes and the living body are in the contact state or the living body and both or either of the electrodes and the living body are in the non-contact state is estimated using an amplifier output during a period $\tau_1$ during which influence from a pulse noise can be sufficiently seen, as illustrated in FIG. 7.

As illustrated in FIGS. 8A to 8C, even when signal switching is performed, no pulse noise occurs when both or either of the electrodes and the living body is/are in the non-contact state. In addition, even when both of the pair of electrodes 10a and 10b are in the contact state, a pulse noise, although exhibiting large values immediately after a signal switching in the signal switching unit 3, decreases to a small value after plentiful time has elapsed since the signal switching. Thus, a portion of an amplifier output during a period $\tau_1$ during which influence from a pulse noise can be sufficiently seen, that is, a period $\tau_1$ until a predetermined time has elapsed since a switching timing t, is used as an amplifier output at a timing at which a pulse noise is anticipated to occur, and the contact state is estimated using an amplifier output value at an arbitrary timing within the period $\tau_1$.

The estimation of a contact state is performed by the contact state estimating unit 8 in FIG. 1. Specifically, the contact state estimating unit 8 acquires an amplifier output value included in a period $\tau_1$ as illustrated in FIGS. 8A to 8C and, when the amplifier output value is greater than or equal to a certain threshold value, estimates that the electrodes 10a and 10b are in the contact state. When the amplifier output value is less than the threshold value, the contact state estimating unit 8 estimates that both or either of the electrodes 10a and 10b is/are in the non-contact state.

The period $\tau_1$ is, for example, set at a value less than or equal to 0.1 seconds, preferably set at a value less than or equal to 0.05 seconds, and more preferably set at a value less than or equal to 0.01 seconds.

In FIGS. 8A to 8C, the abscissa and FIGS. 8A, 8B, and 8C indicate time t, amplifier output, measurement phases, and acquisition timings of A/D converted amplifier output values, respectively.

The control unit 6 outputs switching signals to the signal switching unit 3 at timings of switching between the measurement phase 1 and the measurement phase 2 and therewith accumulates switching time information in the data accumulating unit 7 at output timings of the switching signals. Amplifier output values converted into digital values by the A/D converter 5 are successively accumulated in the data accumulating unit 7 in association with A/D conversion time information.

The contact state estimating unit 8 successively reads measurement data accumulated in the data accumulating unit 7, that is, A/D converted values of amplifier output values, and specifies measurement phase switching timings, based on the switching time information. The contact state estimating unit 8 extracts an A/D converted value of an amplifier output value within each period from one of the specified measurement phase switching timings t until a preset, predetermined time has elapsed, based on the A/D conversion time information.

The above "predetermined time", which defines a period within which an A/D converted value is extracted, is set at a value less than or equal to the period $\tau_1$, which is detected in advance as a period during which influence from a pulse noise can be sufficiently seen.

The contact state estimating unit 8 compares the extracted A/D converted value of an amplifier output value with a preset threshold value and determines that the electrodes 10a and 10b are in the contact state when the A/D converted value of the amplifier output value is greater than or equal to the threshold value and determines that both or either of the electrodes 10a and 10b is/are in the non-contact state when the A/D converted value is less than the threshold value. The contact state estimating unit 8 performs the determination of whether the electrodes 10a and 10b are in the contact state or both or either of the electrodes 10a and 10b is/are in the non-contact state for each measurement phase switching timing and outputs a determination result in association with measurement data (that is, A/D converted values of amplifier output values) to the outside via the output unit 9.

By referring to the determination result and measurement data output from the output unit 9, a user determines whether or not measurement data accumulated in the data accumulation unit 7 are measurement data when the electrodes 10a and 10b are in the contact state. When the user, for example, performs analysis of collected measurement data, the user compares the determination result on the contact state and the A/D conversion time information with measurement data and performs the analysis, using, among the measurement data, only measurement data in a period during which the determination result on the contact state determines that the electrodes 10a and 10b are in the contact state. Because of this configuration, it is possible to avoid the analysis from being performed based on measurement data measured in a period during which both or either of the electrodes 10a and 10b is/are in the non-contact state.

As described above, the contact state estimating device 1 in the first embodiment of the present invention is configured to determine whether or not the electrodes 10a and 10b are in the contact state with the object 11 to be measured using data during a period during which influence from a pulse noise occurring due to signal switching is clearly seen instead of data during a period during which influence from the pulse noise has sufficiently subsided.

For this reason, it is possible to determine whether or not the electrodes 10a and 10b are in the contact state with high accuracy. In addition, such a pulse noise occurring at the switching timing of the measurement phases is a noise that occurs in association with switching of the measurement phases and is hard to be influenced by a state of the object 11 to be measured, such as a state of the skin of a human body, size of the electrodes 10a and 10b, and the like. For this reason, it is possible to determine the contact state with higher accuracy regardless of change in the contact state between the object 11 to be measured and the electrodes 10a and 10b, and the like.

The estimation of a contact state by the contact state estimating unit 8 is not limited to a case where the contact state is determined based on a single value of an output signal at an arbitrary time within a period $\tau_1$, and it may be configured to estimate the contact state, based on a plurality of values of an output signal from the amplifier 4 at a plurality of times.

An example of a case where the contact state is estimated based on values of an amplifier output at a plurality of times is illustrated in FIGS. 9A to 9C. In FIGS. 9A to 9C, the abscissa and FIGS. 9A, 9B, and 9C indicate time, amplifier output, measurement phases, and acquisition timings of an A/D converted output signal from the amplifier 4, respectively.

In the example illustrated in FIGS. 9A to 9C, values of the amplifier output at time points before and after each measurement phase switching timing are extracted and a difference therebetween is used.

As illustrated in FIGS. 9A to 9C, when it is assumed that, in a case where the electrodes 10a and 10b are in the contact state, a time point earlier than a measurement phase switching timing t (n), that is, an arbitrary time point in a period from a time point at which a period $\tau_l$, during which a pulse noise has large values, has elapsed since the previous switching timing to a time point t(n), at which a measurement phase is switched is denoted by t(n−1), and an arbitrary time point in a period from the switching timing t(n) until a period $\tau_i$ has elapsed is denoted by t(n+1), an amplifier output value at the time point t(n+1) is greater than an amplifier output value at the time point t(n−1) because a pulse noise has occurred at the time point t(n+1).

Therefore, when an A/D converted value of the amplifier output value at the time point t(n−1) and an A/D converted value of the amplifier output value at the time point t(n+1) are approximately the same, both or either of the electrodes 10a and 10b can be considered to be in the non-contact state. On the other hand, when the A/D converted value of the amplifier output value at the time point t(n+1) is greater than the A/D converted value of the amplifier output value at the time point t(n−1) and a difference therebetween is greater than or equal to a threshold value, the electrodes 10a and 10b can be considered to be in the contact state.

In this case, the control unit 6 switches the measurement phases at a preset timing and, in conjunction therewith, outputs timing signals to the A/D converter 5 at the time point t(n−1), a preset, predetermined time earlier than the measurement phase switching timing t(n), and the time point t(n+1), a preset, predetermined time later than the switching timing t(n), outputs A/D conversion time information, and accumulates A/D converted values of the amplifier output values at the time points t(n−1) and t(n+1) and the A/D conversion time information in association with each other in the data accumulating unit 7. The control unit 6 performs this processing at every switching timing t(n) and accumulates measurement data for a predetermined period of time.

The contact state estimating unit 8 reads measurement data accumulated in the data accumulating unit 7, extracts an amplifier output value at a time point t(n−1), a preset, predetermined time earlier than a measurement phase switching timing t(n), and an amplifier output value at a time point t(n+1), a preset, predetermined time later than the switching timing t(n), based on the A/D conversion time information, and calculates a difference therebetween. The predetermined time between the time points t(n) and t(n−1) is set at a value that enables an amplifier output value in which a pulse noise that occurred in association with a switching of the measurement phases at the previous timing to the switching timing t(n) had been sufficiently reduced to be obtained. The predetermined time between the time points t(n) and t(n+1) is set at a value that enables an amplifier output value when a pulse noise that occurs in association with a switching of the measurement phases at the switching timing t(n) is sufficiently large to be obtained.

The contact state estimating unit 8, for each switching timing t(n), extracts an amplifier output value at the time point t(n−1), the predetermined time earlier than the switching timing t (n), and an amplifier output value at the time point t(n+1), the predetermined time later than the switching timing t(n), and calculates a difference between the amplifier output values. The contact state estimating unit 8 determines that both or either of the electrodes 10a and 10b is/are in the non-contact state when the difference is less than or equal to a preset threshold value θ and determines that the electrodes 10a and 10b are in the contact state when the difference is greater than the threshold value θ. The threshold value θ is set at a value that enables a determination that the difference between the amplifier output values is sufficiently large and a pulse noise has occurred. The threshold value θ is, for example, preset and stored in the data accumulating unit 7.

This configuration enables whether the electrodes 10a and 10b are in the contact state or both or either of the electrodes 10a and 10b is/are in the non-contact state to be determined. Thus, performing analysis and the like using only amplifier output values during a period during which the electrodes 10a and 10b are determined to be in the contact state, based on times at which the electrodes 10a and 10b are determined to be in the contact state, which can be obtained from the A/D conversion time information associated with amplifier output values at the times of this determination, and the A/D conversion time information associated with the amplifier output values enables avoidance of performing the analysis based on incorrect amplifier output values obtained when both or either of the electrodes 10a and 10b is/are in the non-contact state.

Estimation of a contact state in the contact state estimating unit 8 may be determined from a correlation between amplifier output values during different intervals.

Figure 11A:
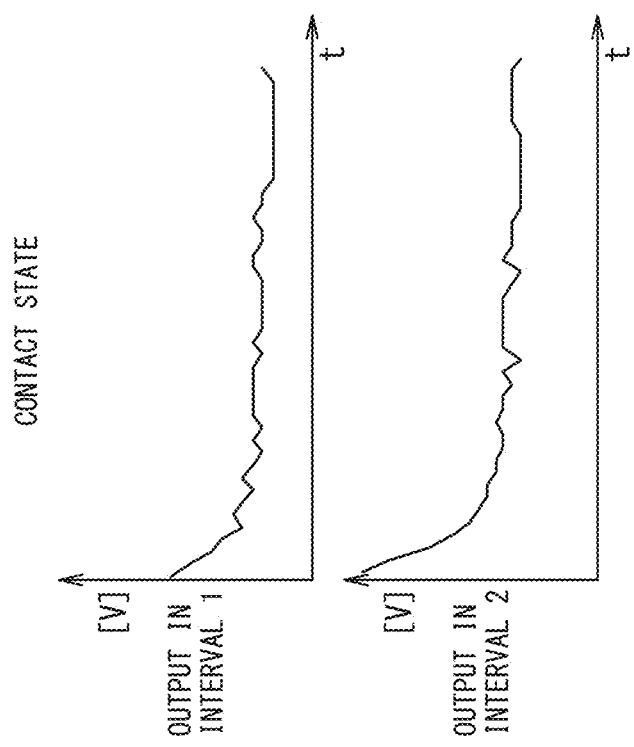
FIGS. 11A and 11B are other explanatory diagrams for a description of the still another estimation method of a contact state.

That is, as illustrated in FIGS. 10A and 10B, in a case where both or either of the electrodes 10a and 10b is/are in the non-contact state with the object 11 to be measured, when it is assumed that an interval from a measurement phase switching timing t11 to the next switching timing t12 and an interval from the measurement phase switching timing t12 to the next switching timing t13 are referred to as an interval 1 and an interval 2, respectively, the amplifier output in the intervals 1 and 2 has random noise components as dominant components as illustrated in, for example, FIG. 11A. On the other hand, in a case where the electrodes 10a and 10b are in the contact state with the object 11 to be measured, when it is assumed that an interval from a measurement phase switching timing t21 to the next switching timing t22 and an interval from a time point t23, which is the next measurement phase switching timing to the time point t22, to the next switching timing t24 are referred to as an interval 11 and an interval 12, respectively, the amplifier output in the intervals 11 and 12 has pulse noises as dominant components because both the intervals 11 and 12 include pulse noises.

When there occurs no random noise, both or either of the electrodes 10a and 10b may be determined to be in the non-contact state when fluctuation in amplifier output values is less than or equal to a certain threshold value.

Thus, when a correlation between the amplifier output values in the intervals 1 and 2 and a correlation between the amplifier output values in the intervals 11 and 12 are taken, the correlation between the amplifier output values in the intervals 11 and 12, both of which include pulse noises and during both of which the electrodes 10a and 10b are in the contact state, has a higher value than the correlation between the amplifier output values in the intervals 1 and 2, neither of which includes a pulse noise and during both of which both or either of the electrodes 10a and 10b is/are in the non-contact state.

Therefore, the electrodes 10a and 10b can be considered to be in the contact state when a correlation value between amplifier output values in two different intervals is greater than or equal to a threshold value and both or either of the electrodes 10a and 10b can be considered to be in the non-contact state when the correlation value is less than the threshold value. The threshold value is set at a value that enables a determination that the correlation value is sufficiently large and pulse noises have occurred. The threshold value θ is, for example, preset and stored in the data accumulating unit 7.

Intervals for which a correlation value is obtained may be successive intervals defined by measurement phase switching timings (for example, the intervals 1 and 2) or isolated intervals (for example, the intervals 11 and 12). Length of intervals for which a correlation value is obtained may be the same length or different length. That is, a correlation value may be configured to be obtained between amplifier output values in one measurement phase and three measurement phases.

Figure 11B:
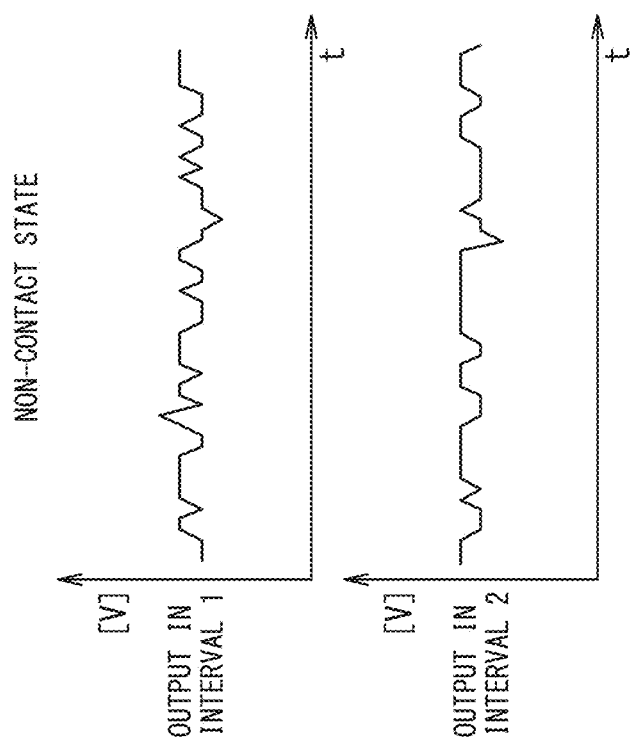

In FIGS. 10A and 10B, the abscissa and FIGS. 10A and 10B indicate time, amplifier output, and measurement phases, respectively. In FIGS. 11A and 11B, the abscissa and the ordinate represent time and amplifier output, respectively.

Estimation of a contact state in the contact state estimating unit 8 may be determined by storing a reference waveform S1 that simulates a waveform including a pulse noise in the data accumulating unit 7 in advance and comparing a correlation value between a waveform of an amplifier output in an interval from a measurement phase switching timing to the next switching timing and the reference waveform S1 with a predetermined threshold value.

Figure 13A:
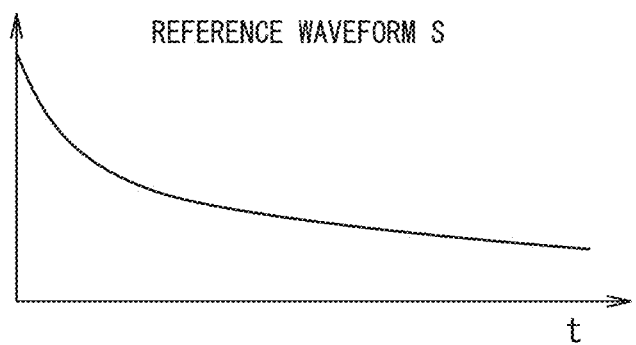
FIGS. 13A to 13C are other explanatory diagrams for a description of the still another estimation method of a contact state.
Figure 13B:
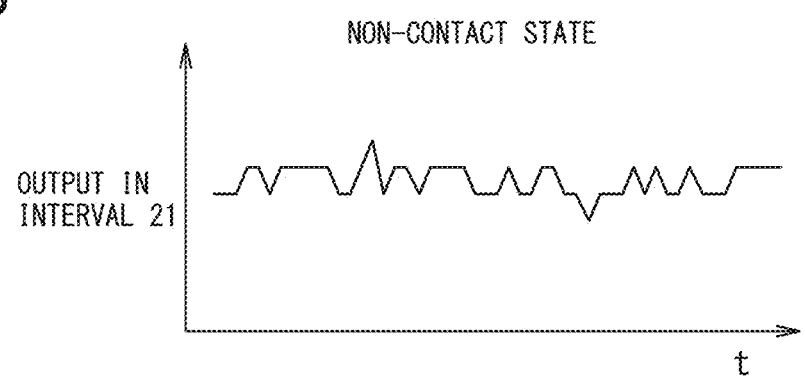
Figure 13C:
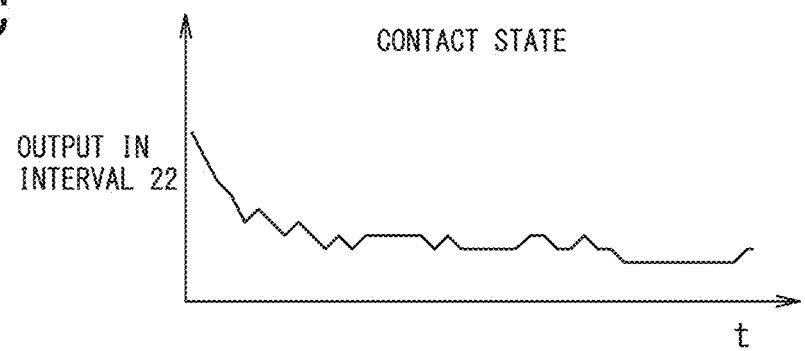

That is, it is assumed that, as illustrated in FIGS. 12A and 12B, an interval from a measurement phase switching timing t31 to the next switching timing t32 when both or either of the electrodes 10a and 10b is/are in the non-contact state with the object 11 to be measured and an interval from a measurement phase switching timing t41 to the next switching timing t42 when the electrodes 10a and 10b are in the contact state are referred to as an interval 21 and an interval 22, respectively. When a waveform, illustrated in FIG. 13A, that gently decreases is used as a reference waveform S and a correlation value between amplifier output values in the interval 21, illustrated in FIG. 13B, and the reference waveform S and a correlation value between amplifier output values in the interval 22, illustrated in FIG. 13C, and the reference waveform S are obtained, the amplifier output values in the interval 22 have a higher correlation value. Therefore, for example, it may be configured that a correlation value between a waveform of an amplifier output during an interval from a measurement phase switching timing to the next switching timing and the reference waveform S is calculated at an arbitrary timing, such as for every interval and for every other interval, and, when the correlation value is greater than or equal to a preset threshold value, the electrodes 10a and 10b are determined to be in the contact state.

As described above, when estimation of a contact state is configured to be determined from a correlation between amplifier output values during different intervals, it is also possible to determine whether or not the electrodes 10a and 10b are in the contact state with high accuracy.

Even when estimation of a contact state is determined from a correlation between amplifier output values during different intervals, as with the method described above, it may be configured to obtain a correlation value between the reference waveform S during a measurement phase and a waveform of the amplifier output during a single measurement phase or to obtain a correlation value between the reference waveform S during a measurement phase and a waveform of the amplifier output during a plurality of (for example, three) measurement phases.

Second Embodiment

Next, a second embodiment of the present invention will be described.

The second embodiment is a contact state estimating device that, in the contact state estimating device 1 in the first embodiment, is configured to further estimate contact stability using amplifier output. The contact stability is an index based on fluctuation in contact area between electrodes 10a and 10b and an object 11 to be measured.

For example, when the electrodes 10a and 10b are in contact with the object 11 to be measured, such as the skin, moving a region where the electrodes 10a and 10b are attached causes contact area between the electrodes 10a and 10b and the object 11 to be measured to fluctuate, which further causes contact resistance between the object 11 to be measured and the electrodes 10a and 10b to fluctuate. That is, in FIG. 6, resistance $R_{c1}$ and $R_{c2}$ fluctuate. When the skin, which is the object 11 to be measured, is dry or fluctuation in the contact area between the object 11 to be measured and the electrodes 10a and 10b is minute, fluctuation in the resistance $R_{c1}$ and $R_{c2}$ is small and it is thus sometimes difficult to detect the fluctuation.

However, using an amplifier output during a period from a measurement phase switching timing until a period $\tau_1$ has elapsed, that is, an amplifier output during a period during which a pulse noise occurs, enables fluctuation in the contact area to be detected with high accuracy. Hereinafter, the reason for the above capability will be described.

Fluctuation in the contact resistance between the object 11 to be measured and the electrodes 10a and 10b causes fluctuation in the amplifier output to increase. Fluctuation in the amplifier output associated with the fluctuation in the contact resistance also occurs in a pulse noise and, in particular, notably appears as fluctuation in a peak value of the pulse noise.

That is, when the electrodes 10a and 10b are attached to a human body serving as the object 11 to be measured, fluctuation in the contact resistance causes the amplifier output to fluctuate and, in particular, peak values of the amplifier output to notably fluctuate in intervals during which pulse noises occur, as illustrated in FIG. 14A. On the other hand, when fluctuation in the contact resistance is small, the amplifier output after every measurement phase switching timing fluctuates in a similar manner in an interval between measurement phase switching timings and fluctuation in amplifier output values corresponding to peaks of pulse noises is small, as illustrated in FIG. 14B.

Thus, by use of fluctuation in peak values of pulse noises, the contact resistance is determined to be fluctuating, that is, the contact stability is determined to be unstable, when the fluctuation in the peak values is greater than a threshold value.

As illustrated in FIGS. 14A and 14B, it is assumed that consecutive measurement phase switching timings are denoted by $t_p1, t_p2, \ldots,$ and $t_pN$ (N is a positive integer) and A/D converted values of amplifier output values at time points at which a certain time $t_r$ has elapsed since the respective measurement phase switching timings $t_pN$ are denoted by s1, s2, ..., and sN. The certain time $t_r$ is set at, for example, an elapsed time from a measurement phase switching timing to a time point at which the amplifier output reaches a peak value of a pulse noise.

With respect to respective measurement phase switching timings, the A/D converted values s1, s2, ..., and sN of the amplifier output values at time points at which the certain time tτ has elapsed since the measurement phase switching timings $t_pN$ are acquired as values equivalent to peak values of pulse noises.

With respect to the acquired A/D converted values s1 to sN of the amplifier output values with respect to respective measurement phase switching timings, fluctuation width V is detected, and, when the A/D converted values fluctuate with the fluctuation width V exceeding a preset threshold value, the contact stability is determined to be unstable. As the fluctuation width V, for example, a difference value between a maximum value and a minimum value of the A/D converted values sN for every certain period or a variance value for every certain period may be used. In addition, the fluctuation width V for every certain period may be calculated using, for example, amplitude values of the A/D converted values sN after high-pass filter processing, and any other method may be applied as long as being able to calculate the fluctuation width V.

With regard to a detection result of the contact stability, the fluctuation width V may be output as a value representing the contact stability, or a value to which the fluctuation width V is converted may be output as an index indicating the contact stability. In addition, it may be configured that a threshold value for the fluctuation width V is set, the contact state is determined to be unstable when the fluctuation width V is greater than or equal to the threshold value, and the determination result is output, and the determination method is not limited to a specific one.

In addition, it can be configured that the estimation of the contact stability is performed by a contact state estimating unit 8 and a result therefrom is output by an output unit 9.

Third Embodiment

Next, a third embodiment of the present invention will be described.

Figure 15:
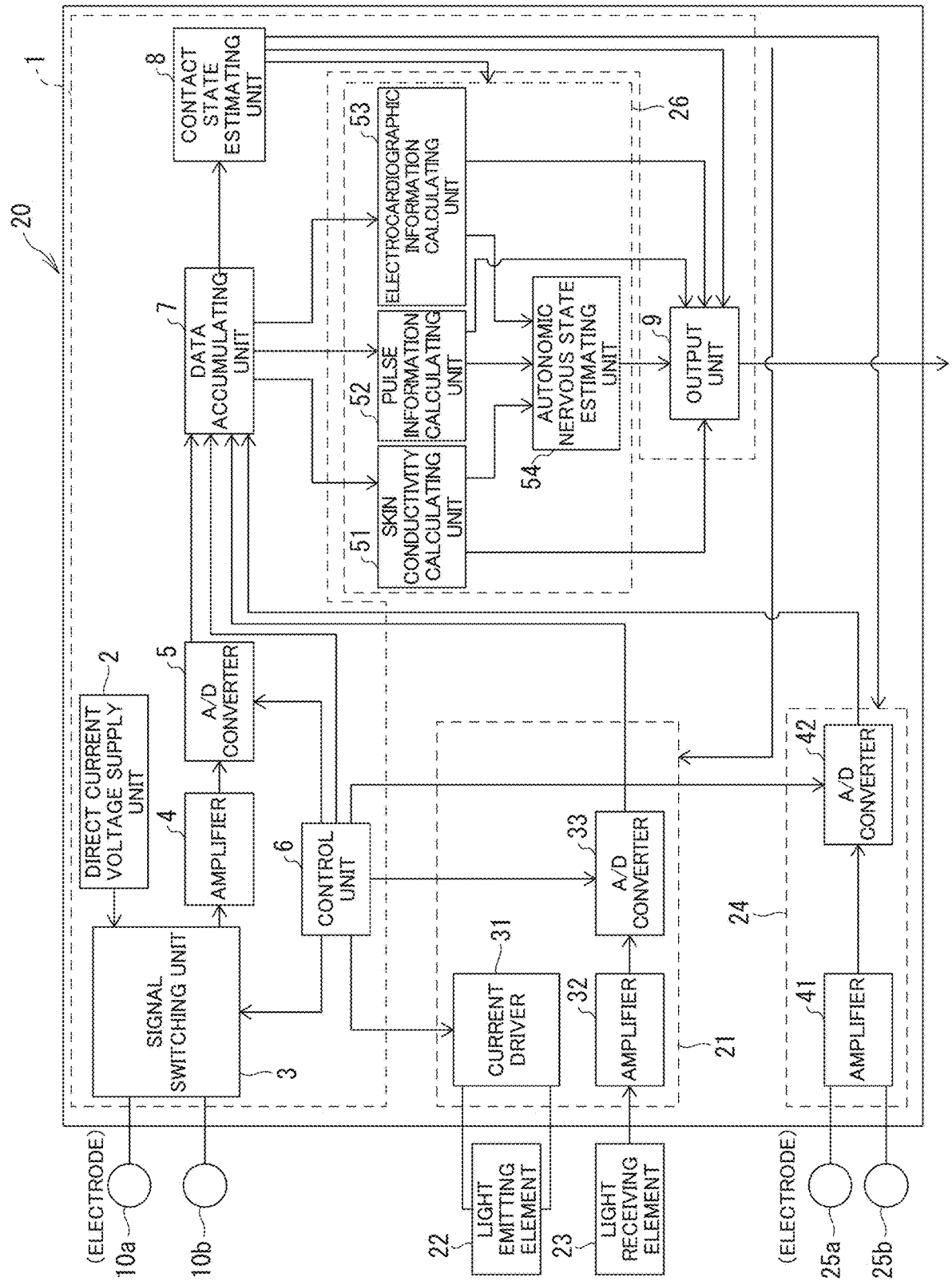
FIG. 15 is a block diagram illustrative of an example of a biological signal measuring device according to a third embodiment of the present invention.

The third embodiment is an embodiment in which the contact state estimating device 1 according to the second embodiment of the present invention is applied to a biological signal measuring device. FIG. 15 is a block diagram illustrative of an example of a biological signal measuring device 20 according to the present invention. The same signs are assigned to constituent elements having the same functions as constituent elements of the contact state estimating device 1 illustrated in FIG. 1.

As illustrated in FIG. 15, the biological signal measuring device 20 includes a contact state estimating device 1 illustrated in FIG. 1, a pulse wave signal acquiring unit 21, a light emitting element 22 and a light receiving element 23 for pulse wave signal acquisition, an electrocardiographic signal acquiring unit 24, a pair of electrodes 25a and 25b for electrocardiographic signal acquisition, and a biological information output unit 26.

The pulse wave signal acquiring unit 21 includes a current driver 31 that drives the light emitting element 22, an amplifier 32 that amplifies a detected signal from the light receiving element 23, and an A/D converter 33 that A/D converts output from the amplifier 32. The current driver 31 is driven in response to a driving signal from a control unit 6 in the contact state estimating device 1, supplies the light emitting element 22 with current, and makes the light emitting element 22 emit light and irradiate an object 11 to be measured with the light. The light receiving element 23 receives reflected light that is light emitted from the light emitting element 22 and reflected by the object 11 to be measured and outputs a current signal having intensity according to the amount of received light to the amplifier 32. The amplifier 32 amplifies the current signal from the light receiving element 23. The A/D converter 33 accepts input of a timing signal instructing execution of A/D conversion on output from the amplifier 32 from the control unit 6 and the output from the amplifier 32, converts the output from the amplifier 32 to a digital signal at a timing at which the timing signal is input by the control unit 6, and outputs the digital signal to a data accumulating unit 7. The output from the amplifier 32 that has been converted to a digital signal is accumulated in the data accumulating unit 7 in association with A/D conversion time information, to be described later, that is input from the control unit 6 to the data accumulating unit 7 and represents a time at which the control unit 6 output a timing signal to the A/D converter 33.

In association with pulsation of the object 11 to be measured, such as a human body, the amount of reflected light that is light emitted by the light emitting element 22 and reflected by the object 11 to be measured temporally fluctuates. Thus, pulse information can be obtained from fluctuation information of the amount of light received by the light receiving element 23.

The electrocardiographic signal acquiring unit 24 includes an amplifier 41 that is connected to electrodes 25a and 25b and an A/D converter 42 that A/D converts output from the amplifier 41. The electrodes 25a and 25b are electrodes for measuring an electrocardiographic signal and are attached in contact with the object 11 to be measured.

The amplifier 41 includes a differential amplifier, an analog filter, and the like and performs amplification and noise elimination of a signal input from the electrodes 25a and 25b and outputs a processed signal to the A/D converter 42. The A/D converter 42 accepts input of a timing signal instructing execution of A/D conversion on output from the amplifier 41 from the control unit 6 and the output from the amplifier 41, converts the output from the amplifier 41 to a digital signal at a timing at which the timing signal is input by the control unit 6, and outputs the digital signal to the data accumulating unit 7. The output from the amplifier 41 that has been converted to a digital signal is accumulated in the data accumulating unit 7 in association with A/D conversion time information, to be described later, that is input from the control unit 6 to the data accumulating unit 7 and represents a time at which the control unit 6 output a timing signal to the A/D converter 42.

The A/D conversion time information associated with output from the A/D converter 33, the A/D conversion time information associated with output from the A/D converter 42, and the A/D conversion time information associated with output from the A/D converter 5 may be the same or different from one another. That is, timings at which A/D conversion is performed in the A/D converter 33, the A/D converter 42, and the A/D converter 5 may be the same timing or different timings.

The biological signal measuring device 20 is configured to indicate time series relationships between estimation results of whether or not the electrodes are in a contact state and each of the output from the A/D converter 33 (that is, a pulse wave signal) and the output from the A/D converter 42 (that is, an electrocardiographic signal) through associating the A/D conversion time information with each of the output from the A/D converters 33 and 42.

Discrimination of data respectively output from the A/D converter 5 included in the contact state estimating device 1, the A/D converter 33 included in the pulse wave signal acquiring unit 21, and the A/D converter 42 included in the electrocardiographic signal acquiring unit 24 from one another is achieved by, for example, storing tag information of the data from the respective A/D converters in the data accumulating unit 7.

The biological information output unit 26 includes a skin conductivity calculating unit 51, a pulse information calculating unit 52, an electrocardiographic information calculating unit 53, and an autonomic nervous state estimating unit 54.

The skin conductivity calculating unit 51 calculates skin conductivity from data accumulated in the data accumulating unit 7 and outputs the calculated skin conductivity to the outside via an output unit 9.

The skin conductivity calculating unit 51 calculates skin conductivity and outputs the calculated skin conductivity only when an estimation result by the contact state estimating device 1 is input and the electrodes are determined to be in the contact state and a stable contact state. Alternatively, the skin conductivity calculating unit 51 may also output an estimation result by the contact state estimating device 1 in conjunction with skin conductivity. The skin conductivity calculating unit 51, for example, specifies amplifier output values during a period during which the electrodes are determined to be in the contact state and the stable contact state, based on A/D conversion time information associated with amplifier output values when the electrodes are determined to be in the contact state and the stable contact state and, based on the specified amplifier output values, calculates skin conductivity.

The pulse information calculating unit 52 extracts, among the data accumulated in the data accumulating unit 7, data at a plurality of times that were output from the A/D converter 33 in the pulse wave signal acquiring unit 21 and A/D conversion time information, calculates a pulse rate and the like, and outputs the calculated pulse rate and the like to the outside via the output unit 9. The pulse information calculating unit 52, for example, specifies pulse wave signals output from the A/D converter 33 during a period during which the electrodes are determined to be in the contact state and the stable contact state, based on A/D conversion time information associated with amplifier output values when the electrodes are determined to be in the contact state and the stable contact state and, based on the specified pulse wave signals, calculates a pulse rate and the like.

The electrocardiographic information calculating unit 53 extracts, among the data accumulated in the data accumulating unit 7, data at a plurality of times that were output from the A/D converter 42 included in the electrocardiographic signal acquiring unit 24 and A/D conversion time information, calculates a heart rate and the like, and outputs the calculated heart rate and the like to the outside via the output unit 9. The electrocardiographic information calculating unit 53, for example, specifies electrocardiographic signals output from the A/D converter 42 during a period during which the electrodes are determined to be in the contact state and the stable contact state, based on A/D conversion time information associated with amplifier output values when the electrodes are determined to be in the contact state and the stable contact state and, based on the specified electrocardiographic signals, calculates a heart rate and the like.

The control unit 6, as with the control unit 6 in the first embodiment, outputs switching signals to a signal switching unit 3 and therewith outputs switching time information to the data accumulating unit 7. The control unit 6 also outputs a driving signal for controlling driving operation by the current driver 31. The control unit 6 also outputs timing signals instructing execution of A/D conversion to the A/D converter 5, the A/D converter 33, and the A/D converter 42 and therewith outputs A/D conversion time information that represents times at which timing signals were output and corresponds to each of the A/D converters 5, 33, and 42 to the data accumulating unit 7.

The control unit 6 does not operate the pulse wave signal acquiring unit 21, the electrocardiographic signal acquiring unit 24, and the biological information output unit 26 when both or either of the electrodes is/are estimated to be in a non-contact state by the contact state estimating unit 8 and operates the pulse wave signal acquiring unit 21, the electrocardiographic signal acquiring unit 24, and the biological information output unit 26 only when the electrodes are estimated to be in the contact state or the stable contact state. This configuration enables incorrect measurement when both or either of the electrodes is/are in the non-contact state or an unstable contact state to be prevented from occurring and therewith enables power consumption to be reduced. For example, it can be configured that, when both or either of the electrodes is/are detected to be in the non-contact state or the unstable contact state by the contact state estimating unit 8, the contact state estimating unit 8 outputs a suspension signal to the pulse wave signal acquiring unit 21, the electrocardiographic signal acquiring unit 24, and the biological information output unit 26, and, when a suspension signal is input from the control unit 6, the pulse wave signal acquiring unit 21, the electrocardiographic signal acquiring unit 24, and the biological information output unit 26 suspend their operation. The pulse wave signal acquiring unit 21, the electrocardiographic signal acquiring unit 24, and the biological information output unit 26 may reduce frequency of acquisition of respective signals instead of suspending their operation.

It can also be configured that, when both or either of the electrodes is/are detected to be in the non-contact state or the unstable contact state, the biological information output unit 26 outputs an estimation result by the contact state estimating unit in conjunction with skin conductivity, pulse information, heartbeat information, and the like.

The autonomic nervous state estimating unit 54 estimates an autonomic nervous state using output from at least one of the skin conductivity calculating unit 51, the pulse information calculating unit 52, and the electrocardiographic information calculating unit 53 and outputs the estimated autonomic nervous state to the outside via the output unit 9. The autonomic nervous state is known to have a correlation with fluctuation in the skin conductivity and fluctuation in the pulse rate and the heart rate, and, when a living body is, for example, brought to a state of sympathetic nerve dominance, the fluctuation in the skin conductivity increases and the fluctuation in the pulse rate and the heart rate decreases. On the other hand, when the living body is brought to a state of parasympathetic nerve dominance, the fluctuation in the skin conductivity decreases and the fluctuation in the pulse rate and the heart rate increases. The autonomic nervous state estimating unit 54 acquires at least one of skin conductivity, pulse information, and heartbeat information from at least one of the skin conductivity calculating unit 51, the pulse information calculating unit 52, and the electrocardiographic information calculating unit 53 and estimates an autonomic nervous state. For calculation of fluctuation in the skin conductivity, for example, differences between two consecutive values among skin conductivity values at a plurality of detection times that are output from the skin conductivity calculating unit 51 or the magnitude of amplitude of alternating components in the skin conductivity may be used, and the calculation method is not limited to a specific one.

The fluctuation in the pulse information and the heartbeat information may, for example, be obtained by using values of the pulse rate and the heart rate at a plurality of detection times that are output from the pulse information calculating unit 52 and the electrocardiographic information calculating unit 53 and a generally used index, such as a stress index LF/HF (LF indicates low frequency components corresponding to the Mayor wave, which is blood pressure fluctuation, and HF indicates high frequency fluctuation components (HF components) corresponding to respiratory fluctuation and the Mayor wave, which is blood pressure fluctuation), and the calculation method is not limited to a specific one.

By estimating an autonomic nervous state using only skin conductivity or pulse information when the electrodes are estimated to be in the contact state or the stable contact state by use of an estimation result from contact state estimation by the contact state estimating unit 8, the biological information output unit 26 can prevent incorrect measurement due to use of values when both or either of the electrodes is/are in the non-contact state or the unstable contact state from occurring.

Although, in the third embodiment, a case where the contact state estimating device in the second embodiment is applied to a biological signal measuring device was described, the contact state estimating device in the first embodiment can also be applied.

Although the third embodiment includes the autonomic nervous state estimating unit 54, the embodiment does not always have to include the autonomic nervous state estimating unit 54. Similarly, the embodiment does not always have to include all of the skin conductivity calculating unit 51, the pulse information calculating unit 52, and the electrocardiographic information calculating unit 53.

Although, in the third embodiment, a case where skin conductivity, pulse information, heartbeat information, an autonomic nervous state, an estimation result of a contact state, and the like are output to the outside via the output unit 9 was described, the embodiment is not limited to the case. By using an output unit having a display function as the output unit 9, further disposing a display unit performing display based on output from the output unit 9 to the biological signal measuring device 20, or the like, it may be configured to, instead of outputting information, such as skin conductivity, pulse information, heartbeat information, an autonomic nervous state, and an estimation result of a contact state, to the outside, display such various types of information including an estimation result of a contact state within the biological signal measuring device 20. Further, such various types of information including an estimation result of a contact state may be configured to be displayed within the biological signal measuring device 20 and therewith output to the outside.

Fourth Embodiment

Next, a fourth embodiment of the present invention will be described.

Figure 16:
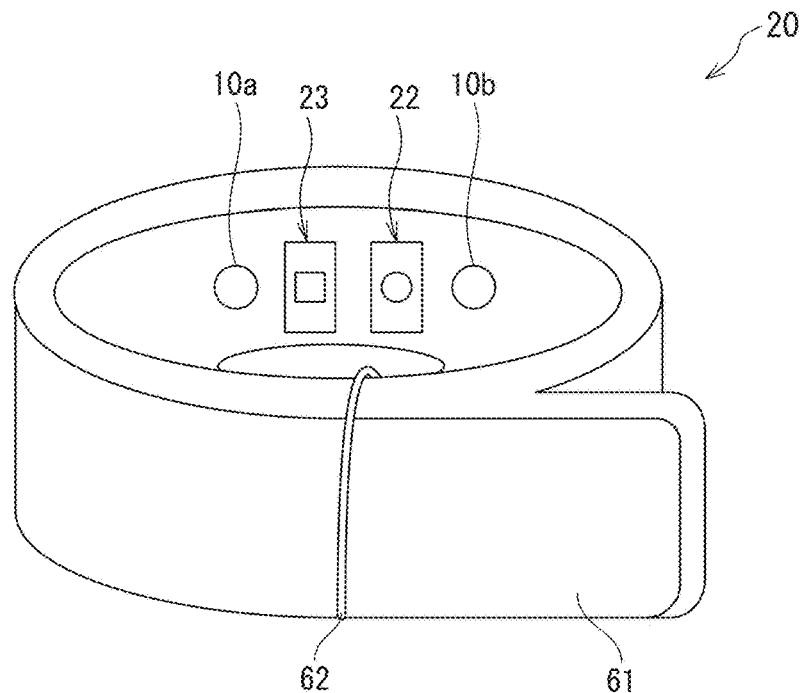
FIG. 16 is a schematic view illustrative of another example of the biological signal measuring device.

The fourth embodiment is a specific example of the biological signal measuring device 20 according to the third embodiment of the present invention. As illustrated in an external view in FIG. 16, the biological signal measuring device 20 is mounted in an arm attachment band 61, and, on the inner side of the arm attachment band 61, a light emitting element 22 and a light receiving element 23 are disposed with a light emitting surface and a light receiving surface thereof exposed and electrodes 10a and 10b are further disposed on both sides of the light emitting element 22 and the light receiving element 23. The arm attachment band 61 is designed to be attached to an arm of a human body with the light emitting element 22, the light receiving element 23, and the electrodes 10a and 10b in contact with the skin of the human body by wrapping the arm attachment band 61 around the arm in such a way that the light emitting element 22, the light receiving element 23, and the like face the human body and adjusting length of the arm attachment band 61 with a fixture 62.

This configuration enables biological information, such as skin conductivity, pulse information, heartbeat information, and an autonomic nervous state, when the biological signal measuring device 20 is in contact with or in stable contact with a human body and information, such as contact stability when such measured biological information is acquired, to be output.

Fifth Embodiment

Next, a fifth embodiment of the present invention will be described.

The fifth embodiment is the same as the second to fourth embodiments except that an estimation method of a contact state is different from those of the contact state estimating devices 1 in the second to fourth embodiments.

Figure 17:
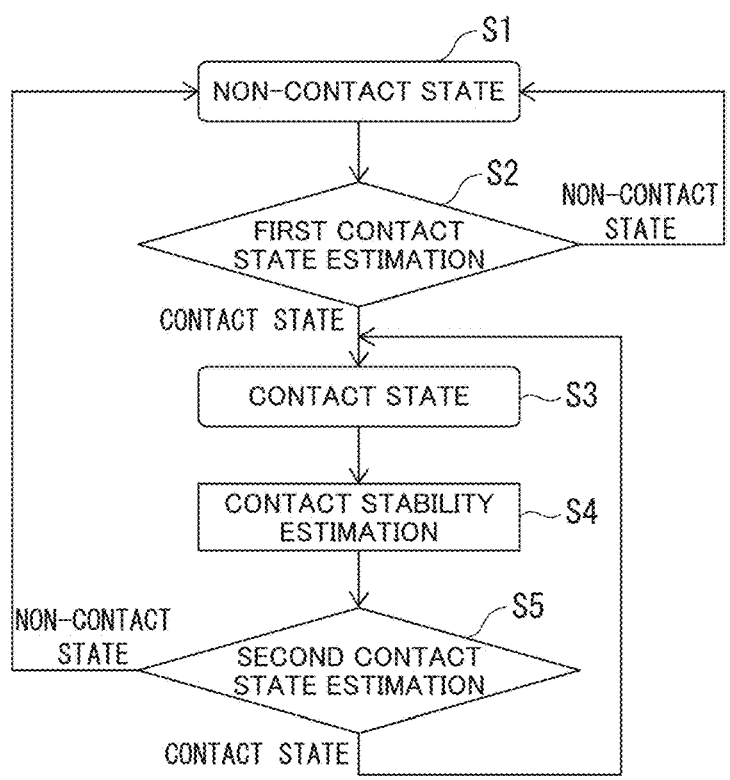
FIG. 17 is a flowchart descriptive of an example of a contact state estimating method.

To a contact state estimating unit 8 of a contact state estimating device 1 in the fifth embodiment, an amplifier output converted to a digital signal is input. As illustrated in FIG. 17, starting from, for example, a state in which both or either of electrodes is/are determined to be in a non-contact state (step S1), first contact state estimation is performed (step S2). The first contact state estimation is processing of comparing an A/D converted value of the amplifier output with a threshold value θ1. When the A/D converted value of the amplifier output is less than the threshold value θ1, both or either of the electrodes is/are determined to be in the non-contact state and the process returns to step S1, and processing, such as outputting the determination result, is performed. When the A/D converted value of the amplifier output is greater than or equal to the threshold value θ1, the electrodes are determined to be in a contact state and the process proceeds to step S3, and, after processing, such as outputting the determination result, is performed, the process proceeds to step S4 and contact stability estimation is performed. In the contact stability estimation, stability determination is performed in accordance with, for example, a procedure similar to that in the third embodiment, and, after processing, such as outputting the determination result, is performed, the process proceeds to step S5 and second contact state estimation is performed.

The second contact state estimation is processing of comparing an A/D converted value of the amplifier output with a threshold value θ2. When the A/D converted value of the amplifier output is less than the threshold value θ2, both or either of the electrodes is/are determined to be in the non-contact state and the process proceeds to step S1, and processing, such as outputting the determination result, is performed. When the A/D converted value of the amplifier output is greater than or equal to the threshold value θ2, the electrodes are determined to be in the contact state and the process proceeds to step S3. The threshold value θ2 may be the same value as the threshold value θ1 in the first contact state estimation or a value satisfying θ2>θ1. Setting the threshold values θ1 and θ2 in such a way as to satisfy θ2>θ1 enables a state that has been determined to be the contact state to be hard to transition to a state that is determined to be the non-contact state. Conversely, setting the threshold values θ1 and θ2 in such a way as to satisfy θ2<θ1 enables a state that has been determined to be the non-contact state to be hard to transition to a state that is determined to be the contact state.

The estimation of a contact state in the contact state estimating unit 8 may be performed in accordance with steps illustrated in FIG. 18.

That is, starting from a state that is the non-contact state (step S11), the process proceeds to step S12, and loop processing from step S12 to step S14 is repeatedly performed a preset number i of times.

That is, first, first contact state estimation is performed, and an estimation result A is stored in a predetermined storage area (step S13). The first contact state estimation is performed in a similar manner to the processing in step S2 in FIG. 17.

Next, the process proceeds to step S14, and whether or not the estimation result from the first contact state estimation in step S13 and the estimation result from the first contact state estimation in step S13 at a time point one period before the present time point are the same is determined. When the two estimation results are the same, the process returns from step S15 to step S13, and the number of repetitions of the loop processing is incremented and the loop processing is repeated. On the other hand, when, in the determination in step S14, the two estimation results are not the same, the process returns to step S12, and the number of repetitions of the loop processing is reset to one and the loop processing from step S12 to step S15 is repeated again.

When the loop processing from step S12 to step S15 has been repeated i times consecutively, that is, when the estimation in step S13 has resulted in the same result i times consecutively, the process proceeds to step S16, and, when the estimation results are the non-contact state, both or either of the electrodes is/are determined to be in the non-contact state, the process proceeds to step S11, and processing, such as outputting the determination result, is performed. On the other hand, when the estimation results are the contact state, the electrodes are determined to be in the contact state and the process proceeds to step S17, and, after processing, such as outputting the determination result, is performed, contact stability estimation is performed (step S18). The contact stability estimation is performed in a similar manner to the processing in step S4 in FIG. 17.

Next, the process proceeds to step S19, and loop processing from step S19 to step S22 is repeatedly performed a preset number j of times.

That is, first, second contact state estimation is performed, and an estimation result B is stored in a predetermined storage area (step S20). The second contact state estimation is performed in a similar manner to the processing in step S5 in FIG. 17.

Next, the process proceeds to step S21, and whether or not the estimation result from the second contact state estimation in step S20 and the estimation result from the second contact state estimation in step S20 at a time point one period before the present time point are the same is determined. When the two estimation results are the same, the process returns from step S22 to step S19, and the number of repetitions of the loop processing is incremented and the loop processing is repeated. On the other hand, when, in the determination in step S21, the two estimation results are not the same, the process returns to step S19, and the number of repetitions of the loop processing is reset to one and the loop processing from step S19 to step S22 is repeated again.

When the loop processing from step S19 to step S22 has been repeated j times consecutively, that is, when the estimation in step S21 has resulted in the same result j times consecutively, the process proceeds to step S23, and, when the estimation results are the non-contact state, both or either of the electrodes is/are determined to be in the non-contact state, the process proceeds to step S11. On the other hand, when the estimation results are the contact state, the electrodes are determined to be in the contact state and the process proceeds to step S17, and, after processing, such as outputting the determination result, is performed, the process proceeds to step S18.

Repeating the first contact state estimation and the second contact state estimation and, when the same result is obtained a predetermined number of times consecutively, employing the obtained estimation result as a determination result indicating a situation of contact of electrodes 10a and 10b, as described above, enable estimation accuracy to be improved. The numbers i and j of repetitions of the first contact state estimation and the second contact state estimation may be the same number or different numbers. For example, setting the number j of repetitions of the second contact state estimation greater than the number i of repetition of the first contact state estimation enables a state that has been determined to be the contact state to be hard to transition to a state that is determined to be the non-contact state. Conversely, setting the number i of repetition of the first contact state estimation greater than the number j of repetition of the second contact state estimation enables a state that has been determined to be the non-contact state to be hard to transition to a state that is determined to be the contact state.

When it is assumed that frequency at which the first contact state estimation is performed and frequency at which the second contact state estimation is performed are denoted by f1 (times/sec) and f2 (times/sec), respectively, f1 and f2 may be the same value or different values. For example, setting the frequency values in such a way as to satisfy f1<f2 enables a state that has been determined to be the contact state to be hard to transition to a state that is determined to be the non-contact state.

Sixth Embodiment

Next, a sixth embodiment of the present invention will be described.

Figure 19:
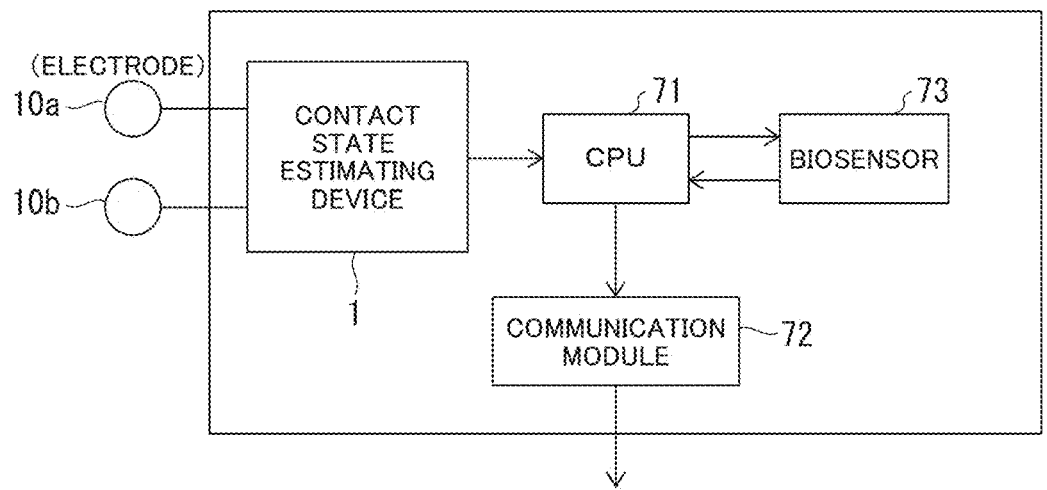
FIG. 19 is a block diagram illustrative of still another example of the biological signal measuring device.

FIG. 19 is a block diagram illustrative of an example of a biological signal measuring device 20 according to the sixth embodiment.

The biological signal measuring device 20 according to the sixth embodiment includes a contact state estimating device 1, a central processing unit (CPU) 71, such as a processor unit, a communication module 72, and a biosensor 73.

The contact state estimating device 1 in the sixth embodiment estimates a contact state, and a contact state estimating unit 8 of the contact state estimating device 1 outputs an estimation result from the contact state estimation to the central processing unit 71.

The biosensor 73 acquires a biological signal and outputs the acquired biological signal to the central processing unit 71. Examples of the biosensor 73 include a pulse wave sensor including a light emitting element 22, a light receiving sensor 23, a current driver 31, an amplifier 32, and an A/D converter 33 in FIG. 15. The biosensor 73 may be a biosensor of any other type, such as an electrocardiographic sensor, in addition to a pulse wave sensor and may include one or a plurality of biosensors.

The central processing unit 71 outputs an input signal from the biosensor 73 to the communication module 72, and the communication module 72 processes the input data into a data form conforming to a predetermined communication protocol and outputs the processed data. Analyzing the data output from the communication module 72 separately with an analyzer and the like enables biological information to be estimated.

The central processing unit 71 also transmits an instruction of transition to a sleep state or return to an operating state to the biosensor 73 and the communication module 72, based on an estimation result from the contact state estimation performed by the contact state estimating device 1.

Figure 20:
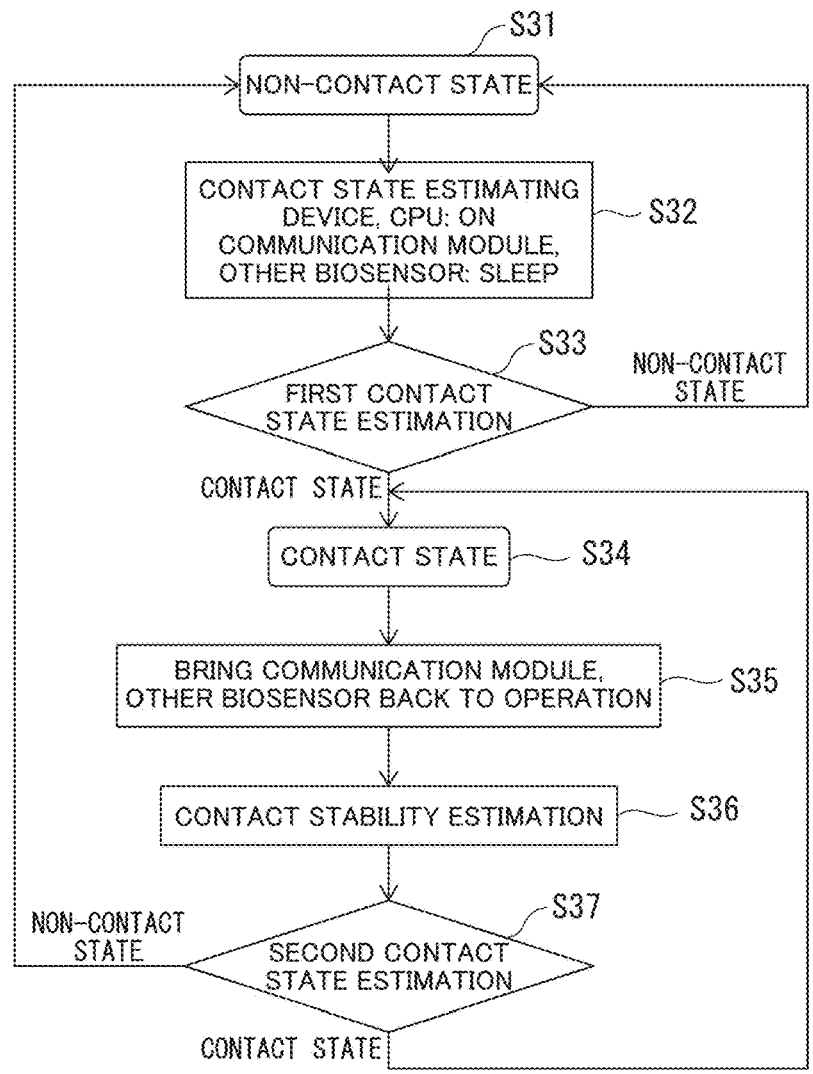
FIG. 20 is a flowchart descriptive of an example of an operation of the biological signal measuring device.

FIG. 20 is a flowchart illustrative of an example of processing steps performed by the central processing unit 71.

As illustrated in FIG. 20, the central processing unit 71 successively inputs estimation results estimated and transmitted by the contact state estimating device 1 and, when a state in which both or either of electrodes is/are in a non-contact state (step S31) has continued for a certain period, makes only the contact state estimating device 1 operate and switches the communication module 72 and the biosensor 73 to a sleep state (step S32). When the state in which both or either of the electrodes is/are in the non-contact state has not continued for a certain period, the central processing unit 71 keeps the communication module 72 and the biosensor 73 in an operating state without switching the communication module 72 and the biosensor 73 to the sleep state.

The central processing unit 71 performs first contact state estimation (step S33) and, when both or either of the electrodes is/are determined to be in the non-contact state in the first contact state estimation, returns to step S31 and, when the electrodes are determined to be in a contact state in the first contact state estimation, determines that the electrodes are brought to the contact state (step S34), proceeds to step S35, and switches the communication module 72 and the biosensor 73, which have been in the sleep state, to the operating state. The first contact state estimation performed in step S33 is performed in a similar manner to the first contact state estimation performed in the processing in step S2 in FIG. 17.

Subsequently, the central processing unit 71 performs contact stability estimation (step S36). The contact stability estimation is performed in a similar manner to the contact stability estimation performed in the processing in step S4 in FIG. 17. An estimation result from the contact stability estimation is, for example, output to the outside in conjunction with data from the biosensor 73.

Next, the central processing unit 71 proceeds to step S37 and performs second contact state estimation. The second contact state estimation is performed in a similar manner to the second contact state estimation performed in the processing in step S5 in FIG. 17. When the second contact state estimation results in a determination that the electrodes are in the contact state, the central processing unit 71 returns to step S34, and, when the second contact state estimation results in a determination that both or either of the electrodes is/are in the non-contact state, the central processing unit 71 returns to step S31.

Since, as described above, when, in the first contact state estimation, it is determined that both or either of the electrodes is/are brought to the non-contact state, the central processing unit 71 switches the biosensor 73, the communication module 72, and the like to the sleep state, it is possible to reduce power consumption by an amount equivalent to operation of the biosensor 73, the communication module 72, and the like. In addition, since, in the first contact state estimation, the contact state estimating device 1, using a plurality of estimation results from repetitions of the contact state estimation for a certain length of period, determines whether or not both or either of the electrodes is/are brought to the non-contact state, it is possible to avoid incorrectly determining that both or either of the electrodes is/are brought to the non-contact state or the contact state although both or either of the electrodes was/were temporarily brought to the non-contact state or the contact state and to avoid frequently repeating the sleep state and return to the operating state.

Estimating contact stability through the contact stability estimation enables reliability of an output signal from the biosensor 73 to be estimated from information of the contact stability.

Figure 21:
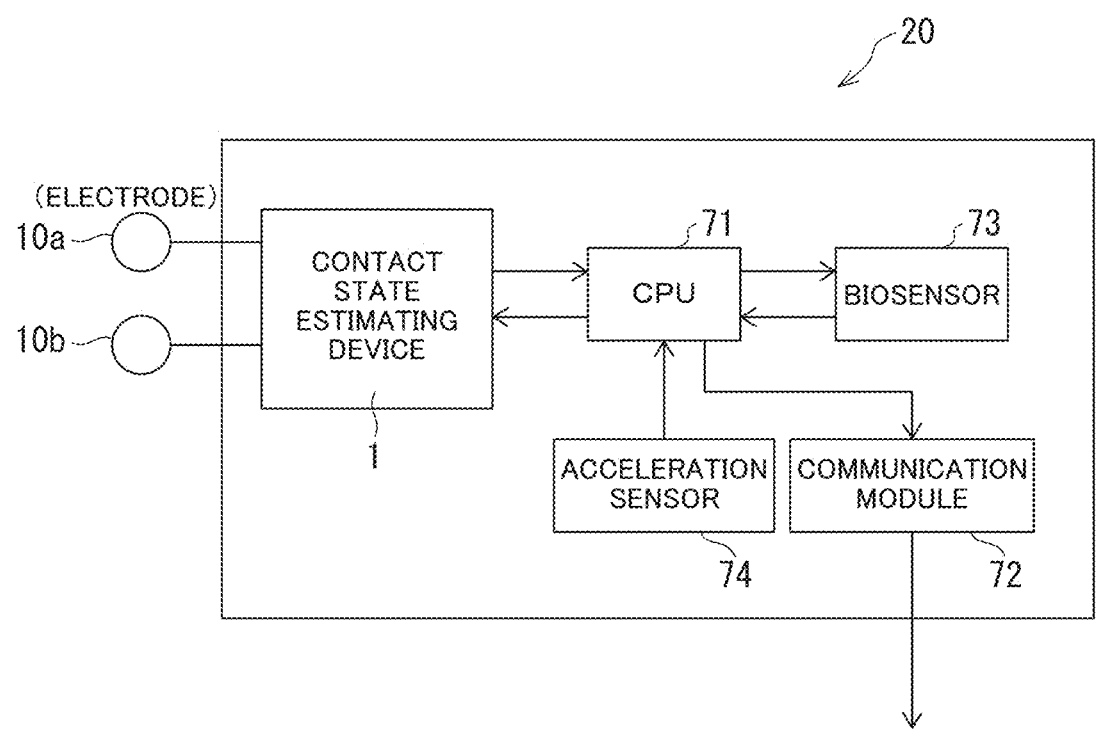
FIG. 21 is a block diagram illustrative of still another example of the biological signal measuring device.

To the biological signal measuring device according to the sixth embodiment described above, an acceleration sensor 74 may be further disposed, as illustrated in FIG. 21.

The acceleration sensor 74 detects acceleration of the biological signal measuring device 20 and outputs the detected acceleration to the central processing unit 71 as an acceleration signal. The central processing unit 71 switches frequencies of measurement by the contact state estimating device 1 according to an acceleration signal input from the acceleration sensor 74.

Figure 22:
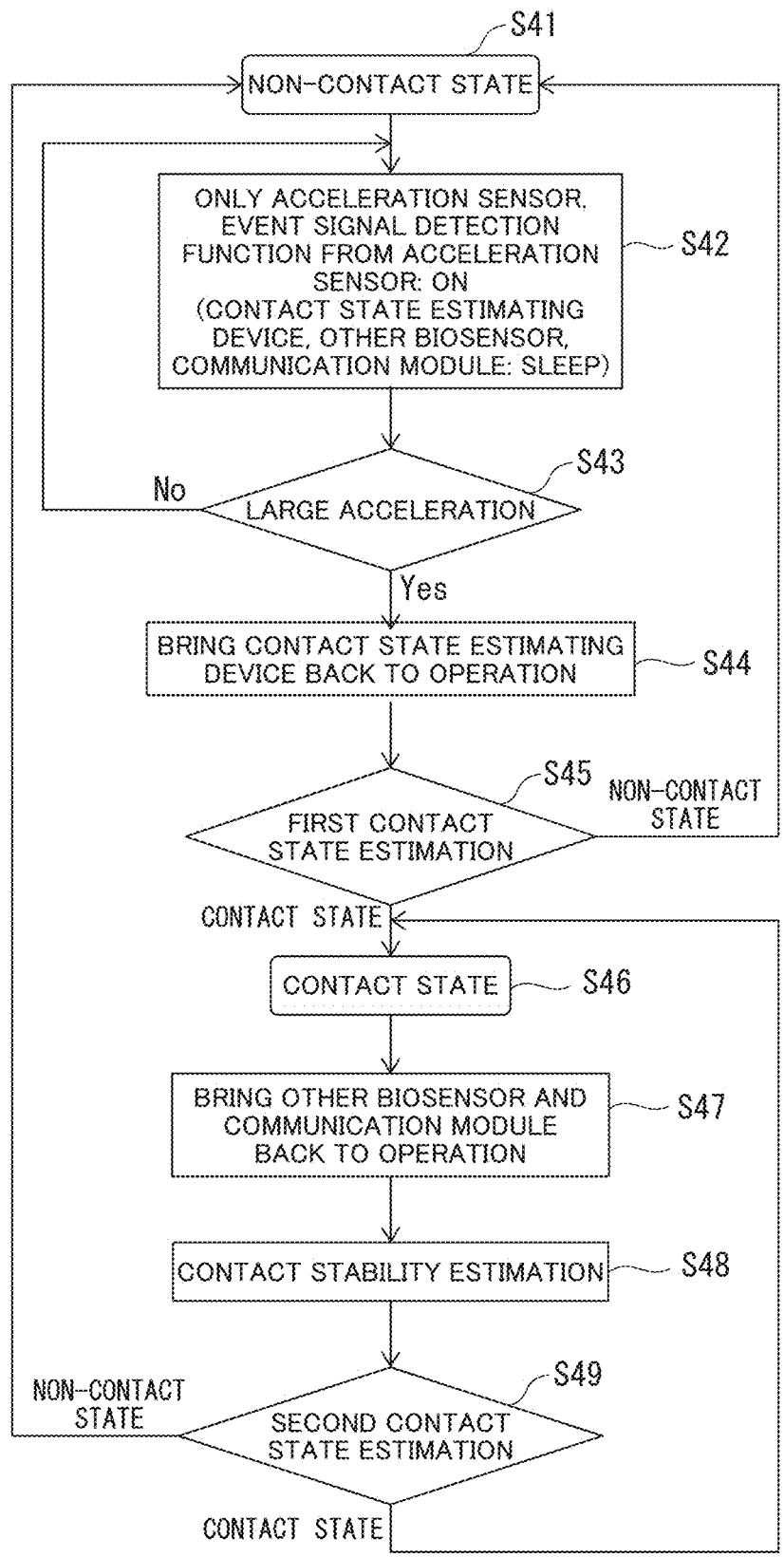
FIG. 22 is a flowchart descriptive of an example of another operation of the biological signal measuring device.

FIG. 22 is a flowchart illustrative of an example of processing steps performed by the central processing unit 71.

As illustrated in FIG. 22, the central processing unit 71 successively accepts input of estimation results estimated and transmitted by the contact state estimating device 1 and, when a state in which both or either of electrodes is/are in the non-contact state (step S41) has continued for a certain period, switches the communication module 72, the biosensor 73, and the functions of the contact state estimating device 1, the acceleration sensor 74, the central processing unit 71, and the like except a detection function of an event signal from the acceleration sensor 74 to an operation suspended state or a reduced measurement frequency state (step S42).

Next, the central processing unit 71 proceeds to step S43 and, when an acceleration signal from the acceleration sensor 74 is lower than a preset threshold value, returns to step S42 and, when the acceleration signal is higher than or equal to the threshold value, proceeds to step S44 and brings only the contact state estimating device 1 back to the operating state. Subsequently, the central processing unit 71 performs the first contact state estimation, based on an estimation result by the contact state estimating device 1 in a similar manner to the processing in step S33 in FIG. 20 (step S45) and, when the first contact state estimation results in a determination that the contact state estimating device 1 is in the non-contact state, returns to step S41. On the other hand, when the first contact state estimation results in a determination that the contact state estimating device 1 is in the contact state, the central processing unit 71 proceeds to step S46, determines that the contact state estimating device 1 is in the contact state and proceeds to step S47, brings the respective units, such as the biosensor 73 and the communication module, that are in the sleep state back to the operating state, and subsequently performs the contact stability estimation in a similar manner to the processing in step S36 in FIG. 20 (step S48). Subsequently, the central processing unit 71 performs the second contact state estimation in a similar manner to the processing in step S37 in FIG. 20 (step S49) and, when the second contact state estimation results in a determination that the contact state estimating device 1 is in the contact state, returns to step S46 and, when the second contact state estimation results in a determination that the contact state estimating device 1 is in the non-contact state, returns to step S41 and brings the respective units and functions except the acceleration sensor 74 and the detection function of an event signal from the acceleration sensor 74 to the operation suspended state or the reduced measurement frequency state again.

The magnitude of acceleration detected by the acceleration sensor 74 may be, for example, the square sum of the magnitudes of the detected signal in the three axis directions, that is, the directions along the x-axis, the y-axis, and the z-axis that intersect one another at right angles, the sum of absolute values of the magnitudes of the signal along the respective axes, or the magnitude of fluctuation in acceleration, and the calculation method is not limited to a specific one.

As described above, the biological signal measuring device 20 is configured to determine whether or not an acceleration signal from the acceleration sensor 74 is greater than or equal to a threshold value, determine that the biological signal measuring device 20 is attached to a human body when the acceleration signal is greater than or equal to the threshold value, conversely determine that there is a possibility that the biological signal measuring device 20 is not attached to the human body when the acceleration signal is less than the threshold value, and operate the contact state estimating device 1 only when the biological signal measuring device 20 is determined to be attached to the human body. That is, the biological signal measuring device 20 is configured to, first, roughly determine an attachment state of the biological signal measuring device 20 by use of the acceleration sensor 74 and, next, determine whether or not the biological signal measuring device 20 is in contact with the skin of the human body by means of the contact state estimating device 1, and it is therefore possible to more finely determine whether or not to operate the respective units in the biological signal measuring device 20, switch the respective units to an operating state or a sleep state, and, consequently, reduce power consumption.

Seventh Embodiment

Next, a seventh embodiment of the present invention will be described.

The seventh embodiment is an embodiment in which the contact state estimating device 1 according to the first and second embodiments of the present invention is applied to an electrocardiograph.

Figure 23:
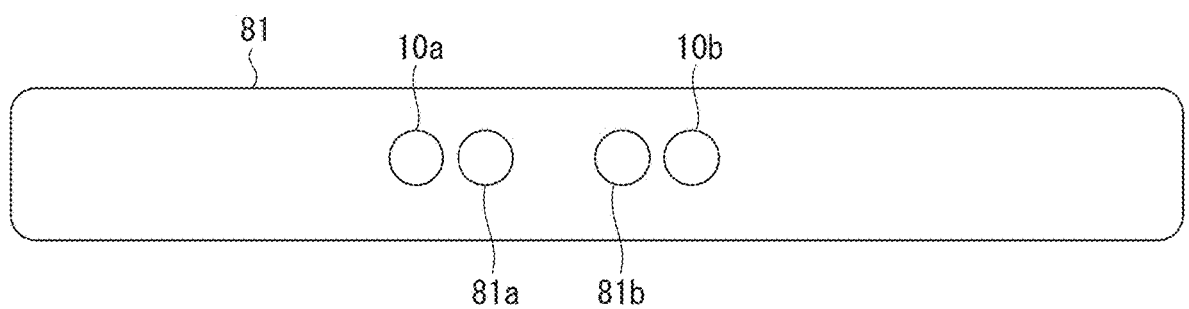
FIG. 23 is a schematic view illustrative of an example of an electrocardiograph to which the biological signal measuring device is mounted.

In FIG. 23, a reference sign 81 indicates a belt unit for attachment to a living body, such as the chest, and reference signs 81a and 81b indicate electrodes for electrocardiogram measurement, and the electrodes 81a and 81b for electrocardiogram measurement are arranged with a space interposed therebetween in the longitudinal direction of the belt unit 81 and, on both sides in the longitudinal direction of the electrodes 81a and 81b for electrocardiogram measurement, electrodes 10a and 10b for contact state detection are disposed.

Application of the contact state estimating device 1 to an electrocardiograph in this way enables a contact state of the electrocardiograph with a human body to be estimated accurately. It may be configured that the electrodes 81a for electrocardiogram measurement and the electrode 10a for contact state detection are combined into a common electrode and, in a similar manner, the electrode 81b for electrocardiogram measurement and the electrode 10b for contact state detection are combined into a common electrode and measurement is performed switching functions thereof with switches temporally.

The electrocardiograph can be applied to an arbitrary region of a human body, such as the chest, the head, the abdomen, the leg portion, the arm portion, and the neck, as a measurement region, and similar effects can be obtained with respect to any of the regions.

The electrodes 10a and 10b for contact state detection may be dedicated electrodes for contact state detection and, further, may be configured to be used as both electrodes for contact state detection and electrodes for biological signal detection, such as skin conductivity measurement and electrocardiogram measurement, and to be thereby able to detect various types of biological signals, such as skin conductivity and electrocardiogram measurements.

Although it is preferable that electrode shapes of the electrodes for contact state detection can be arbitrarily set and the two electrodes for contact state detection have substantially the same size, the electrodes do not always have to be limited to the configuration.

In the respective embodiments described above, it is possible to apply the contact state estimating device 1 to, as an object to be measured, a dielectric material other than a living body, and, for example, it is possible to estimate whether or not a moisture meter for vegetables or the like is in contact with a vegetable.

As described above, an embodiment of the present invention enables whether electrodes and a living body are in a contact state or a living body and both or either of the electrodes are in a non-contact state with each other to be determined with high accuracy without being affected by a contact environment, such as a dry state of the skin and size of the electrodes.

Since, as described above, a contact state is estimated based on pulse noise information, it is possible to estimate a contact state with high accuracy without being affected by variation in DC offsets of devices, individual variation in skin conductivity among subjects, and the like as compared with a contact state estimating method using only the magnitude of voltage values.

The contact state estimating device 1 is capable of estimating whether the electrodes and the living body are in a contact state or the living body and both or either of the electrodes are in a non-contact state with a small amount of data in a short period with high accuracy and can be achieved with a small amount of current consumption and a data accumulating unit having a comparatively small capacity.

Measuring biological information only when the electrodes and the living body are in contact with each other or are in a stable contact state enables invalid data during a period during which both or either of the electrodes and the living body are in a non-contact state to be excluded and operation time and power consumption to be reduced.

It is also possible to estimate contact stability with high accuracy, to exclude data collected while contact between the electrodes and the living body is unstable at the time of data analysis, and to achieve improvement in accuracy of analysis using biological information.

In addition, in a conventional measurement device as disclosed in, for example, PTL 3 that is configured to switch pathways through which voltage is applied to two electrodes, changing a processing method of an obtained signal without adding a special mechanism enables not only whether the electrodes and the living body are in a contact state or the living body and both or either of the electrodes are in a non-contact state with high accuracy but also contact stability to be estimated with high accuracy.

Although, in the embodiments described above, the contact state estimating unit 8 is configured to successively determine a contact state, based on a measured amplifier output, the contact state estimating unit 8 may be configured to accumulate amplifier output data for a predetermined period in the data accumulating unit 7 and, after measurement has been completed, perform analysis, based on the accumulated data in the the data accumulating unit 7.

Although, in the embodiments described above, a case where an amplifier output and A/D conversion time information are associated with each other and, based on the A/D conversion time information, an amplifier output corresponding to a pulse noise occurring in association with measurement phase switching is acquired was described, the configuration is not limited to the case. For example, it may be configured that a timing at which a pulse noise has occurred is detected from differential values of an amplifier output and a contact state or contact stability may be estimated considering the detected timing as a measurement phase switching timing, and such a timing may be detected using another method as long as the method is capable of detecting an occurrence timing of a pulse noise occurring in association with measurement phase switching.

Although the embodiments of the present invention were described above, the respective embodiments described above indicate devices and methods for embodying the technical idea of the present invention, and the technical idea of the present invention does not limit materials, shapes, structures, arrangements, and the like of the constituent components to those described in the embodiments above. Various modifications can be made to the technical idea of the present invention within the scope of the technical idea defined by the claims described in CLAIMS.

REFERENCE SIGNS LIST

1 Contact state estimating device
2 Direct current voltage supply unit
3 Signal switching unit
4 Amplifier
5 A/D converter
6 Control unit
7 Data accumulating unit
8 Contact state estimating unit
9 Output unit
10a, 10b Electrode
20 Biological signal measuring device
21 Pulse wave signal acquiring unit
22 Light emitting element
23 Light receiving element
24 Electrocardiographic signal acquiring unit
25a, 25b Electrode
26 Biological information output unit
51 Skin conductivity calculating unit
52 Pulse information calculating unit
53 Electrocardiographic information calculating unit 54 Autonomic nervous state estimating unit
71 Central processing unit (CPU)
72 Communication module
73 Biosensor
74 Acceleration sensor

The invention claimed is:

1. A contact state estimating device comprising:
a first electrode and a second electrode adapted to be brought into contact with a living body serving as an object to be measured;
a direct current voltage supply unit;
a signal switching unit configured to switch between a first pathway and a second pathway, wherein in the first pathway the direct current voltage supply unit supplies direct current voltage to the first electrode and an output signal from the second electrode is output and in the second pathway the direct current voltage supply unit supplies direct current voltage to the second electrode and an output signal from the first electrode is output; and
a contact state estimating unit configured to estimate a contact state of the first electrode or the second electrode with the living body, based on whether a pulse noise occurs or does not occur in the output signal acquired at a predetermined time after a signal switching operation by the signal switching unit to switch between the first pathway and the second pathway,
wherein the contact state estimating unit estimates whether the first electrode and the second electrode are in a contact state, in which both the first and second electrodes are in contact with the living body, or are in a non-contact state, in which both or either of the first and second electrodes are not in contact with the living body.

2. The contact state estimating device according to claim 1, wherein the contact state estimating unit:
estimates that the first electrode and the second electrode are in a contact state when the output signal acquired at the predetermined time is greater than or equal to a predetermined threshold value; and
estimates that both or either of the first electrode and the second electrode is/are in a non-contact state when the output signal is less than the threshold value.

3. The contact state estimating device according to claim 1, wherein the contact state estimating unit:
estimates that the first electrode and the second electrode are in a contact state when a difference value between the output signal output from the signal switching unit at the predetermined time and the output signal output from the signal switching unit at a timing other than the predetermined time is greater than or equal to a predetermined threshold value; and
estimates that both or either of the first electrode and the second electrode is/are in a non-contact state when the difference value is less than the threshold value.

4. The contact state estimating device according to claim 1, wherein the contact state estimating unit estimates whether the first electrode and the second electrode are in a contact state, or both or either of the first electrode and the second electrode is/are in a non-contact state, based on a correlation between values of the output signal output from the signal switching unit during a first interval that is an interval between a first signal switching timing at which the signal switching is performed and a second signal switching timing different from the first signal switching timing and values of the output signal output from the signal switching unit during a second interval that is an interval between a third signal switching timing different from the first signal switching timing and a fourth signal switching timing different from the third signal switching timing.

5. The contact state estimating device according to claim 1, wherein the contact state estimating unit estimates whether the first electrode and the second electrode are in a contact state, or both or either of the first electrode and the second electrode is/are in a non-contact state, based on a correlation between values of the output signal output from the signal switching unit during a first interval that is an interval between a first signal switching timing at which the signal switching is performed and a second signal switching timing different from the first signal switching timing and values of a reference signal.

6. The contact state estimating device according to claim 1, wherein the contact state estimating unit estimates whether the first electrode and the second electrode are in a stable contact state in which contact states of both the first electrode and the second electrode with the living body are stable or in an unstable contact state in which a contact state of the first electrode or the second electrode with the living body is unstable, based on a fluctuation in values of a plurality of the output signals acquired at the predetermined time.

7. The contact state estimating devices according to claim 1, wherein the contact state estimating unit estimates that the first electrode and the second electrode are in the contact state when the pulse noise occurs and that the first electrode and the second electrode are in the non-contact state when the pulse noise does not occur.

8. A biological signal measuring device comprising:
the contact state estimating device according to claim 1;
a biosensor configured to acquire a biological signal from a living body; and
a biological information output unit configured to output biological information, based on the biological signal transmitted by the biosensor.

9. The biological signal measuring device according to claim 8, wherein
the contact state estimating device outputs an estimation result indicating a contact state or a non-contact state to the biological information output unit, and
the biological information output unit performs calculation of the biological information when the estimation result input from the contact state estimating device indicates the contact state.

10. The biological signal measuring device according to claim 8, wherein the biological information output unit does not perform calculation of the biological information when an estimation result input from the contact state estimating device indicates a non-contact state.

11. The biological signal measuring device according to claim 8 comprising:
a control unit configured to output, to the biosensor, an operation instruction to bring the biosensor to an operating state when an estimation result by the contact state estimating device indicates a contact state and output, to the biosensor, an operation suspension instruction to bring the biosensor to an operation suspended state when the estimation result indicates a non-contact state.

12. The biological signal measuring device according to claim 11 comprising:
an acceleration signal acquiring unit configured to acquire an acceleration signal from an acceleration sensor detecting acceleration, wherein the control unit outputs, to the contact state estimating device, a control signal to bring the contact state estimating device to an operation suspended state or a reduced measurement frequency state when a predetermined period has elapsed since the estimation result turned to the non-contact state and output, to the contact state estimating device, a control signal to bring the contact state estimating device to an operating state or a regular measurement frequency state when the acceleration signal acquired by the acceleration signal acquiring unit is greater than or equal to a predetermined threshold value.

13. The biological signal measuring device according to claim 8, wherein
the biosensor is at least one of a pulse wave sensor, an electrocardiographic sensor, and the first electrode and the second electrode of the contact state estimating device, and
the biological information output unit includes at least one of a pulse information calculating unit configured to calculate pulse information that is biological information of the living body, based on a pulse wave signal acquired by the pulse wave sensor, an electrocardiographic information calculating unit configured to calculate electrocardiographic information that is biological information of the living body, based on an electrocardiographic information acquired by the electrocardiographic sensor, and a skin conductivity calculating unit configured to calculate skin conductivity that is biological information of the living body, based on an output signal output from the first electrode and the second electrode.

14. The biological signal measuring device according to claim 8 comprising:
a display unit configured to display biological information of the living body corresponding to the biological signal.

15. A biological signal measuring device comprising:
the contact state estimating device according to claim 6;
a biosensor configured to acquire a biological signal from a living body; and
a biological information output unit configured to output biological information, based on the biological signal transmitted by the biosensor,
wherein
the contact state estimating device outputs an estimation result indicating a stable contact state or an unstable contact state to the biological information output unit, and
the biological information output unit performs calculation of the biological information when the estimation result input from the contact state estimating device indicates the stable contact state.

16. The biological signal measuring device according to claim 15, wherein the biological information output unit does not perform calculation of the biological information when the estimation result input from the contact state estimating device indicates the unstable contact state.

17. The biological signal measuring device according to claim 15 comprising:
a control unit configured to output, to the biosensor, an operation instruction to bring the biosensor to an operating state when the estimation result by the contact state estimating device indicates a contact state or the stable contact state and output, to the biosensor, an operation suspension instruction to bring the biosensor to an operation suspended state when the estimation result indicates the unstable contact state.

18. A contact state estimating method comprising:
for a first electrode and a second electrode configured to be brought into contact with a living body serving as an object to be measured, switching between a first pathway and a second pathway, wherein in the first pathway a direct current voltage supply unit supplies direct current voltage to the first electrode and an output signal from the second electrode is output and in the second pathway the direct current voltage supply unit supplies direct current voltage to the second electrode and an output signal from the first electrode is output;
acquiring the output signal at a predetermined time after a signal switching operation by the signal switching unit to switch between the first pathway and the second pathway; and
based on whether a pulse noise occurs or does not occur in the output signal, estimating a contact state of the first electrode or the second electrode with the living body,
wherein the contact state estimating unit estimates whether the first electrode and the second electrode are in a contact state, in which both the first and second electrodes are in contact with the living body, or are in a non-contact state, in which both or either of the first and second electrodes are not in contact with the living body.

19. A non-transitory medium storing a contact state estimating program causing a computer to perform a contact state estimating method according to claim 18.

* * * * *